US012582584B2

(12) United States Patent
Chen et al.

(10) Patent No.: US 12,582,584 B2
(45) Date of Patent: Mar. 24, 2026

(54) OXIDIZER AND ACID BASED SYSTEM AND REGIMEN FOR ENHANCING SKIN APPEARANCE

(71) Applicant: L'OREAL, Paris (FR)

(72) Inventors: Rebecca Chen, Princeton, NJ (US); Anne-Laure Bernard, New York, NY (US); I-Chien Liao, Princeton, NJ (US); Xi Yan, Berkeley Heights, NJ (US); Rebecca Barresi, Robbinsville, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 17/514,646

(22) Filed: Oct. 29, 2021

(65) Prior Publication Data

US 2023/0136806 A1     May 4, 2023

(51) Int. Cl.
| | |
|---|---|
| *A61K 8/22* | (2006.01) |
| *A61K 8/365* | (2006.01) |
| *A61K 8/368* | (2006.01) |
| *A61Q 19/08* | (2006.01) |

(52) U.S. Cl.
CPC ............... *A61K 8/22* (2013.01); *A61K 8/365* (2013.01); *A61K 8/368* (2013.01); *A61Q 19/08* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 5,693,318 A | 12/1997 | Burke et al. | |
| 5,843,998 A | 12/1998 | Song et al. | |
| 6,071,541 A | 6/2000 | Murad | |
| 6,433,024 B1 | 8/2002 | Popp et al. | |
| 6,573,301 B1 | 6/2003 | Glassman et al. | |
| 6,673,374 B2 | 1/2004 | Murad | |
| 8,715,700 B2 | 5/2014 | Brillouet et al. | |
| 10,130,578 B2 | 11/2018 | Brillouet et al. | |
| 2002/0054918 A1* | 5/2002 | Murad | A61K 33/40 514/474 |
| 2003/0064084 A1 | 4/2003 | Bhagwat et al. | |
| 2003/0224064 A1* | 12/2003 | Kling | A61K 45/06 514/159 |
| 2007/0190008 A1* | 8/2007 | Campain | A61K 8/46 424/70.2 |
| 2008/0020005 A1 | 1/2008 | Chang et al. | |
| 2008/0113037 A1 | 5/2008 | Green et al. | |
| 2011/0240054 A1 | 10/2011 | Pratt et al. | |
| 2015/0018319 A1* | 1/2015 | Larson | A61K 9/0014 206/438 |
| 2019/0125656 A1 | 5/2019 | Chang et al. | |
| 2019/0201304 A1 | 7/2019 | Sverdlove et al. | |

| | | | |
|---|---|---|---|
| 2020/0113797 A1* | 4/2020 | Morgenroth-Ehrich | A61Q 19/007 |
| 2020/0214945 A1* | 7/2020 | Bernard | A61Q 19/02 |
| 2021/0093530 A1 | 4/2021 | Chen et al. | |

FOREIGN PATENT DOCUMENTS

| | | |
|---|---|---|
| CZ | 178196 A3 | 3/1997 |
| EP | 0739209 A1 | 10/1996 |
| EP | 1100454 | 11/2010 |
| FR | 3058053 A1 | 5/2018 |
| GB | 2076286 A | 12/1981 |
| WO | 2000006116 A1 | 2/2000 |
| WO | 2020120513 A1 | 6/2020 |

OTHER PUBLICATIONS

Mike J. Fevola "Ingredient Profile: Salicylic Acid". Cosmetics & Toiletries <https://www.cosmeticsandtoiletries.com/cosmetic-ingredients/actives/blog/21837700/ingredient-profile-salicylic-acid> (Year: 2013).*
Lukic et al. "Formulation of topical acidic products and acidification of the skin—Contribution of glycolic acid" International Journal of Cosmetic Science, vol. 43, Issue 4, p. 419-431, published Apr. 17, 2021, https://doi.org/10.1111/ics.12707.
Search Report issued to French counterpart Application No. FR2200550 dated Oct. 4, 2022.
Anonymous, Mintel, "Cleansing Set," Feb. 10, 2010, XP055967509, No. 1267939, www.gnpd.com.
Anonymous, Mintel, "Fast-Acting Acne Duo," May 12, 2017, XP055967514, No. 4809161, www.gnpd.com.
Anonymous, Mintel, "Over the Moon Set," Nov. 23, 2021, XP055967517, No. 9179094, www.gnpd.com.
PCT Notification of Transmittal of the International Search Report and the Written Opinion of the International Searching Authority, or the Declaration issued to counterpart Application No. PCT/IB2022/060237 dated Feb. 7, 2023.

* cited by examiner

*Primary Examiner* — Nicole P Babson
(74) *Attorney, Agent, or Firm* — McNees Wallace & Nurick

(57) ABSTRACT

A cosmetic skin-enhancing system confers enhanced skin appearance, including improved facial skin brightness, minimized pore appearance, improved visual smoothness and reduced appearance fine lines and wrinkles. The cosmetic skin-enhancing system includes a skin application regimen, and an article of manufacture for using the cosmetic skin-enhancing system, including at least first and second separately contained compositions including an oxidizing component comprising at least one oxidizing agent and water, and a chemical peel component comprising at least one hydroxy-acid and water, each contained to be separately dispensed for application to skin, in any order, and wherein the skin-enhancing system may be used according to any one of a number of possible application regimens wherein the oxidizing component is used in conjunction with the chemical peel component, applied in sequence, once or, or more frequently, with applications of at least one of the components on a daily basis for a few or several days.

21 Claims, 8 Drawing Sheets

OXIDIZER AND ACID BASED SYSTEM AND REGIMEN FOR ENHANCING SKIN APPEARANCE

FIELD OF THE INVENTION

The present invention is generally directed to a cosmetic system for enhancing skin appearance, including improving visual skin brightness and smoothness, minimizing pore appearance, and reducing the appearance fine lines and wrinkles, and a skin-enhancing regimen and article of manufacture for using the cosmetic skin-enhancing system. The skin-enhancing system is especially suited for application to skin anywhere on the body, particularly on facial skin, in some particular embodiments, generally avoiding the skin under and around the eyes.

BACKGROUND OF THE INVENTION

Chemical peels are a non-invasive dermatological products and approaches to improve and treat skin conditions including: photodamaged skin, hyperpigmentation, acne vulgaris, rosacea, premalignant skin cancer, wrinkles and fine lines, superficial scars and the like. These cosmetic compositions include a solution of acids that, when applied topically, penetrate into the skin, inducing and accelerating skin's natural regeneration process by sloughing off dead top layers of skin. The strength and efficacy of a peel is dictated by the formulation, acid type and concentration, which factors affect depth of penetration into the skin. Common chemical peels compositions include one or more of glycolic acid, lactic acid, salicylic acid, and trichloroacetic acid (TCA), among other ingredients. The efficacy of chemical peels is driven by the concentration of hydroxy acids (typically alpha- and beta-hydroxy acids) AHA/BHA and pH of the formula.

Professional-type peels include high levels of acid, for example, greater than 30%, and extreme low pH, typically less than 3, and are typically limited to use with licensed dermatologists and/or aestheticians. The key benefit of professional-type peels is that they confer relatively rapid and significant rejuvenation effects that can include one or more of improved skin radiance/brightness and pore appearance, skin smoothness and reduced fine lines and wrinkles. But professional-type peels can be expensive, are not as convenient as in-home use, and cause relatively high irritation and possible "down time" between applications. At-home-type peels that are used in the home market typically include alpha hydroxy acid (glycolic, lactic acid, mandelic acid, etc.) at a concentration of less than 10%, with a final pH that is greater than 3.0. The key benefits of at-home type peels include consumer convenience and possible cost savings; however, the rejuvenation results normally take around a month to achieve and are typically less impactful than professional-type peels.

A need exists for a skin-enhancing system that provides exceptional and rapid results such as those seen with professional peel compositions, with minimized or no adverse side effects and need for down time as compared with professional peel compositions.

As disclosed herein, the inventors have developed a skin-enhancing system that includes a oxidizing component and a chemical peel component which skin-enhancing system can significantly shorten the time to realize chemical peel benefits as compared with at home peel compositions used alone, and without irritation that is common with professional type peel compositions.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

In various embodiments, compositions are provided for use according to the invention that include oxidizing and chemical peel components, provided for sequential application to skin according to regimens disclosed herein.

In various embodiments, provided is an article of manufacture for a skin-enhancing system comprising at least first and second separately contained compositions, the first composition comprising an oxidizing component, comprising at least one oxidizing agent and water, and the second composition comprising chemical peel component comprising at least one hydroxy-acid and water, wherein the first and second compositions are contained to be separately dispensed for application to skin, in any order, and wherein the skin-enhancing system may be used according to any one of a number of possible embodiments of the inventive skin-enhancing regimen, referred to herein as application cycles, wherein the oxidizing component is used in conjunction with the chemical peel component, applied in sequence, each component applied once daily, or more frequently, with applications of at least one of the components on a daily basis for a few or several days.

In some embodiments, the oxidizing agent in the oxidizing component is selected from the group consisting of hydrogen peroxide, urea peroxide, carbamide peroxide, PVP hydrogen peroxide, and combinations thereof.

In some embodiments, the oxidizing agent in the oxidizing component is present from about 1% to about 10% by weight, based upon the total weight of the oxidizing component.

In some embodiments, the hydroxy acid in the chemical peel component is selected from the group consisting of alpha-hydroxy acids, beta-hydroxy acids, poly-hydroxy acids, and combinations thereof.

In some embodiments, the hydroxy acid in the chemical peel component comprises at least one alpha-hydroxy acid present from about 4% to about 15% by weight, based upon the total weight of the chemical peel component. In one example, the at least one alpha-hydroxy acid comprises lactic acid.

In some embodiments, the hydroxy acid in the chemical peel component further comprises at least one beta-hydroxy acid present from about 0.1% to about 2% by weight, based upon the total weight of the chemical peel component. In one example, the at least one beta-hydroxy acid comprises salicylic acid.

In some embodiments, the hydroxy acid in the chemical peel component further comprises at least one poly-hydroxy acid present from about 4% to about 15% by weight, based upon the total weight of the chemical peel component. In one example, the at least one poly-hydroxy acid comprises gluconolactone.

In some embodiments, the chemical peel component includes two or more hydroxy acids selected from the group consisting of alpha-hydroxy acids, beta-hydroxy acids, poly-hydroxy acids, and combinations thereof.

In some embodiments, the oxidizing agent in the oxidizing component is selected from the group consisting of hydrogen peroxide, urea peroxide, carbamide peroxide, PVP hydrogen peroxide, and combinations thereof, and is present from about 1% to about 10% by weight, based upon the total weight of the oxidizing component, and the oxidizing component further comprises at least one oil, at least one chelating agent, and at least one additional ingredient selected from the group consisting of water based solvents, surfactants, thickeners, pH adjusters, humectants, antioxidants, plant extracts, plant oils, plant butters, fragrances, pearlescent agents, odor absorbers, coloring materials, essential oils, vitamins, antimicrobials, preservatives, and combinations thereof.

In some embodiments, the hydroxy acid in the chemical peel component further comprises at least one beta-hydroxy acid present from about 0.1% to about 2% by weight, or at least one poly-hydroxy acid present from about 4% to about 15% by weight, the amounts based upon the total weight of the chemical peel component, and the chemical peel component further comprises at least one additional ingredient selected from the group consisting of oils, water based solvents, surfactants, thickeners, phenylethyl resorcinol, chelating agents, pH adjusters, humectants, antioxidants, plant extracts, plant oils, plant butters, fragrances, pearlescent agents, odor absorbers, coloring materials, essential oils, vitamins, antimicrobials, preservatives, and combinations thereof.

In some embodiments, each of the oxidizing component and the chemical peel component is provided in a is rinse off or leave on form and is selected from the group consisting of a suspension, an emulsion cream, a serum, an essence, a gel, and a toner.

In some embodiments, one of the oxidizing component and the chemical peel component is a toner and the other is a cream or moisturizer (for example, a creamy emulsion). In some embodiments both of the oxidizing component and the chemical peel component is a toner. And in some embodiments, both of the oxidizing component and the chemical peel component is a cream or moisturizer.

In some embodiments, the article of manufacture comprises the first and second compositions each separately contained in a single use container.

In some embodiments, the article of manufacture comprises the first and second compositions each separately contained in a multi-use container.

In some embodiments, the article of manufacture comprises the first and second compositions each separately contained as single units in a plurality of single use containers.

The invention also provides, in various embodiments, an article of manufacture for the skin-enhancing system comprising at least first and second separately contained compositions.

In some embodiments, the first composition comprises an oxidizing component selected from the group consisting of: at least one oxidizing agent comprising hydrogen peroxide, optionally, one or more agents selected from the group consisting of tetrasodium glutamate diacetate, tetrasodium phosphate, phosphoric acid, sodium phosphate and combinations thereof, and water, wherein the oxidizing component is formulated as a toner; and at least one oxidizing agent comprising hydrogen peroxide, optionally, one or more agents selected from the group consisting of tetrasodium glutamate diacetate, tetrasodium phosphate, phosphoric acid, sodium phosphate and combinations thereof; one or a combination of surfactants including steareth-2 and steareth- 20; one or more polymers including sclerotium gum; one or more vitamin actives, preservatives or combinations thereof; and water present in an amount from about 35% to about 75%, by weight, based on the weight of the oxidizing component, wherein the oxidizing component is formulated as a creamy emulsion.

In some embodiments, the second composition comprises a chemical peel component selected from the group consisting of: (i) hydroxy-acid comprising lactic acid and at least one beta hydroxy acid comprising salicylic acid; one or a combination of oils including squalane and nut oils; one or a combination of surfactants; one or more thickeners; one or more water based solvents comprising glycerin; one or more vitamin actives, preservatives, chelating agents, pH adjusters, or combinations thereof; and water present in an amount from about 40% to about 50%, by weight, based on the weight of the skin peel component, wherein the chemical peel component is formulated as a creamy emulsion; and (ii) hydroxy-acid comprising lactic acid and at least one beta hydroxy acid comprising salicylic acid; one or a combination of oils or plant butters; one or a combination of surfactants including betaine; one or more thickeners including carrageenan; one or more water based solvents comprising glycerin or propanediol; one or more actives including hyaluronic acid, fragrances, preservatives, chelating agents, pH adjusters, or combinations thereof; and water present in an amount from about 40% to about 50%, by weight, based on the weight of the skin peel component, wherein the chemical peel component is formulated as a toner.

In various embodiments, the first and second compositions are contained to be separately dispensed for application to skin, in any order, and wherein the skin-enhancing system may be used according to any one of a number of possible application cycles of the skin-enhancing regimen wherein the oxidizing component is used in conjunction with the chemical peel component, applied in sequence, once or, or more frequently, with applications of at least one of the components on a daily basis for a few or several days.

In some embodiments, each of the first and second compositions is contained as one of a mask, liquid, stick, spray, ointment, paste, foam, mousse, shaving cream, wipe, patch, strip, or film-forming product.

In some embodiments, the first composition is an oxidizing component contained for application as a rinse-off mask, and the second composition is a chemical peel component contained for application as a leave-on cream.

The invention also provides, in various embodiments, a regimen for enhancing skin using oxidizer and acid application components, comprising applying to a region of skin excluding areas of skin around an eye (a) a first composition comprising an oxidizing component that includes an oxidizing agent and water; and (b) a second composition comprising a chemical peel component that includes one or a combination of hydroxy-acids and water, wherein the first and second compositions are applied sequentially, in any order. In some embodiments, the oxidizing component is applied first, followed by the chemical peel component, and in other embodiments, the chemical peel component is applied first, followed by the oxidizing component.

In some embodiments, the steps of the regimen further include (c) rinsing the skin after application of at least one of the first and second compositions, and include (a), (b) and (c) in any order, and wherein the step (c) may be repeated.

The regimen may be selected from one or a combination of application cycles.

The invention also provides, in some embodiments, a regimen for enhancing skin that includes providing a first composition comprising an oxidizing composition selected from the group consisting of: at least one oxidizing agent comprising hydrogen peroxide, optionally, one or more agents selected from the group consisting of tetrasodium glutamate diacetate, tetrasodium phosphate, phosphoric acid, sodium phosphate and combinations thereof, and water, wherein the oxidizing component is formulated as a toner; and at least one oxidizing agent comprising hydrogen peroxide, optionally, one or more agents selected from the group consisting of tetrasodium glutamate diacetate, tetrasodium phosphate, phosphoric acid, sodium phosphate and combinations thereof; one or a combination of surfactants including steareth-2 and steareth-20; one or more polymers including sclerotium gum; one or more vitamin actives, preservatives or combinations thereof; and water present in an amount from about 35% to about 75%, by weight, based on the weight of the oxidizing component, wherein the oxidizing component is formulated as a creamy emulsion; and providing a second composition comprising a chemical peel component selected from the group consisting of: hydroxy-acid comprising lactic acid and at least one beta hydroxy acid comprising salicylic acid; one or a combination of oils including squalane and nut oils; one or a combination of surfactants; one or more thickeners; one or more water based solvents comprising glycerin; one or more vitamin actives, preservatives, chelating agents, pH adjusters, or combinations thereof; and water present in an amount from about 40% to about 50%, by weight, based on the weight of the skin peel component, wherein the chemical peel component is formulated as a creamy emulsion; and hydroxy-acid comprising lactic acid and at least one beta hydroxy acid comprising salicylic acid; one or a combination of oils or plant butters; one or a combination of surfactants including betaine; one or more thickeners including carrageenan; one or more water based solvents comprising glycerin or propanediol; one or more actives including hyaluronic acid, fragrances, preservatives, chelating agents, pH adjusters, or combinations thereof; and water present in an amount from about 40% to about 50%, by weight, based on the weight of the skin peel component, wherein the chemical peel component is formulated as a toner. The regimen further includes applying the first composition to a region of skin excluding areas of skin around an eye; applying the first composition to a region of skin excluding areas of skin around an eye, wherein the first and second compositions are applied sequentially, in any order.

In some embodiments, the steps of the regimen further include (e) rinsing the skin after application of at least one of the first and second compositions, and include (c), (d) and (e) in any order, and wherein the step (e) may be repeated.

In some embodiments, after a first instance of the step of applying the first composition, the step of applying the second composition is repeated once daily, over a plurality of days.

In some embodiments, the step of applying the first composition is repeated once every third, fourth or fifth day and wherein the step of applying the second composition is skipped on the days that the step of applying the first composition is repeated.

In some embodiments, the regimen is practiced for at least 28 days.

In some embodiments, application of the first and second compositions according to the regimen provides synergistic benefits in stimulating cell growth and proliferation as compared with use of the first and second compositions independently.

In some embodiments, application of the first and second compositions according to the regimen results in diminished skin discomfort as compared with use of the first and second compositions independently.

In some embodiments, application of the first and second compositions according to the regimen results in enhanced improvement in skin brightness as compared with use of the first and second compositions independently.

Other features and advantages of the present invention will be apparent from the following more detailed description, by way of example, the principles of the invention.

This disclosure describes exemplary embodiments in accordance with the general inventive concepts and is not intended to limit the scope of the invention in anyway. Indeed, the invention as described in the specification is broader than and unlimited by the exemplary embodiments set forth herein, and the terms used herein have their full ordinary meaning.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

Figure 1:
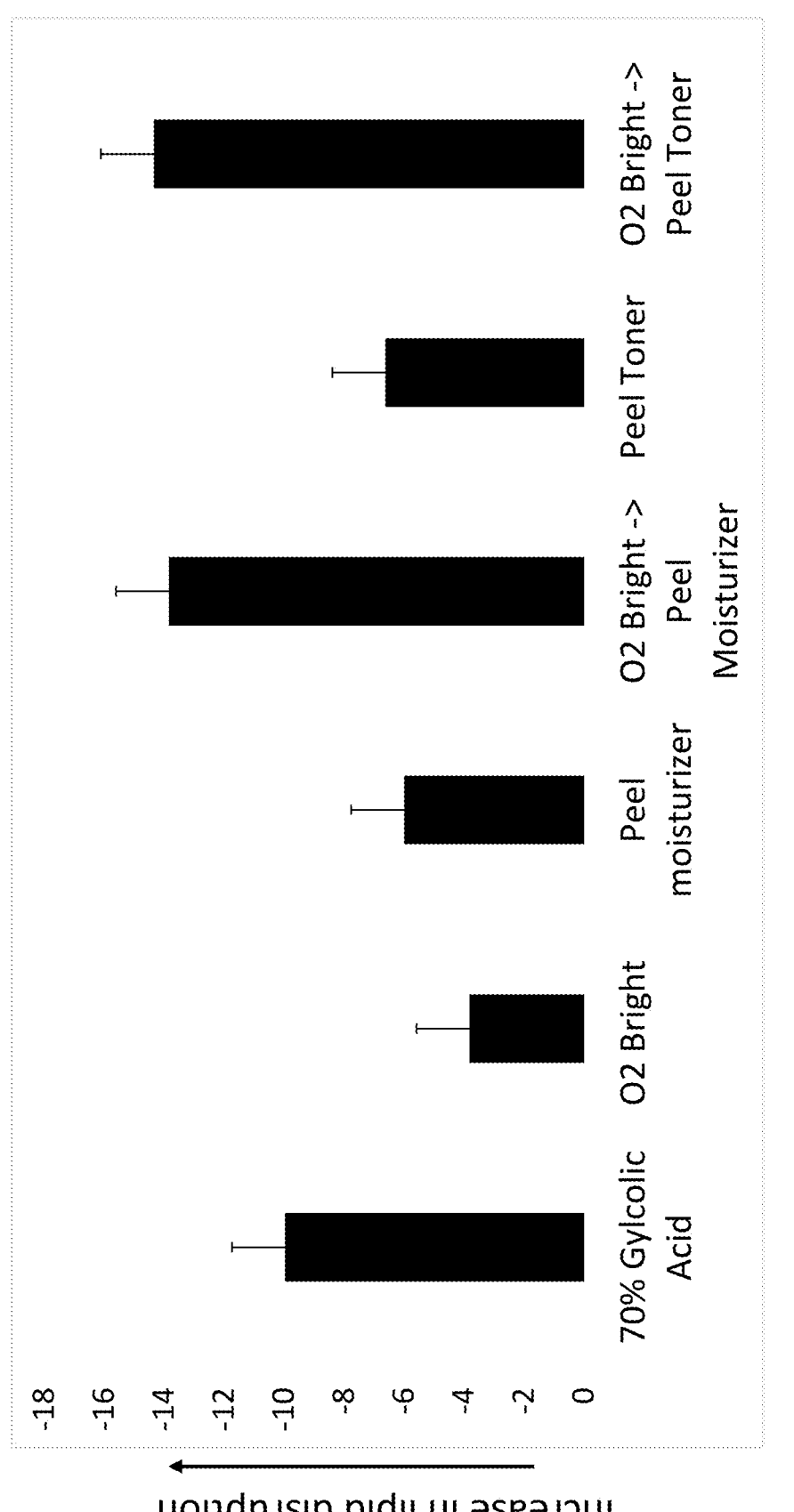
FIG. 1 is a bar graph showing results according to a first study.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

In accordance with the various embodiments, any aspect of any embodiment can be combined or used with any other unless explicitly stated to be exclusive or exclusionary.

DETAILED DESCRIPTION OF THE INVENTION

As used herein, the term "rejuvenation" of skin refers to effects on skin as a result of use of the inventive the skin-enhancing system that can include one or more of improved skin brightness, improved or reduced pore appearance, improved visual skin smoothness and reduced fine lines and wrinkles.

As shown herein, the inventors have provided a skin-enhancing system that includes an oxidizing component, for example a peroxide-containing oxidizing component, and a chemical peel component, for example a hydroxy-acid-containing chemical peel component. Use of the skin-enhancing system confers the benefits of improving brightness, minimizing pore appearance, improving visual skin smoothness and reducing the appearance fine lines and wrinkles. The skin-enhancing system is especially suited for application to skin anywhere on the body, particularly on facial skin, generally avoiding the skin under and around the eyes.

The skin-enhancing system may be used according to any one of a number of possible application cycles of the skin-enhancing regimen wherein the oxidizing component is used in conjunction with the chemical peel component, applied in sequence, once or, or more frequently, with applications of at least one of the components on a daily basis for a few or several days, to significantly improve the speed and extent of rejuvenation of skin as compared to an at-home-type chemical peel used alone. Any of the possible application cycles of the skin-enhancing regimen may be achieved using an article of manufacture that includes each of the oxidizing and chemical peel components packaged in a manner that is suited to the regimen.

Each of the oxidizing component and the chemical peel component can be provided in a form that is rinse off, or a leave on. For example, the oxidizing component may be used in a creamy emulsion form, for example as a rinse-off mask or as a leave-on moisturizer, or in a flowable leave-on toner, and the chemical peel component can likewise be a rinse-off mask, or as a leave-on moisturizer, or in a flowable leave-on toner. In some embodiments, one of the components is a rinse off and the other is a leave on. In some embodiments, both of the components is a rinse off, or both of the components is a leave on.

As exemplified herein, the inventors have shown an in vitro stratum corneum (SC) model for lipid disorganization that the oxidizing component can work as a booster to improve chemical peel efficacy of the chemical peel component, which is evidenced as an increased lipid disorganization in the SC model. More specifically, application of the oxidizing component followed by the chemical peel component, when compared to use of the chemical peel component alone, a consistently higher level of lipid disorganization is observed in the SC studies, regardless of the formulation forms. As shown in the examples, the effects are synergistic in that the effect on SC of the inventive combination of oxidizing component and chemical peel component is greater than the sum of the components when used alone. Further, the results are consistently observed independent of whether either of the components is applied as a rinse-off or leave-on formulation.

In addition, the inventors have shown in a clinical study employing an inventive skin-enhancing regimen that there is more rapid improvement in, brightness, pore appearance, visual skin smoothness, and global facial fine lines and wrinkles, as compared with daily use of the chemical peel component alone. In particular, the inventors have shown that there is detectable improvement in brightness as early as 3 days after starting the regimen, and detectable improvement in global facial fine lines when the aforementioned regimen is followed for fourteen days. In addition, the inventors have also shown that there is a greater improvement in brightness and global facial fine lines when the aforementioned the skin-enhancing regimen is followed for at least one month. The study involved an application cycle of the skin-enhancing regimen including a twice per week application of a rinse off mask form of the oxidizing component and a daily application of a leave-on emulsion moisturizer form of chemical peel component.

While the data provided in the examples were obtained with application of the oxidizing component followed by the chemical peel component, in that order, any sequence of application is acceptable, including at least one application of each of the oxidizing component and the chemical peel component, in alternating sequence. In some particular examples, a skin-enhancing regimen includes application of the chemical peel component at least two or more times, and up to daily applications for a week or more, and application, of the oxidizing component at least one time, and up to -twice a week applications.

These unexpected benefits of skin brightness, visual smoothness, reduced pore size and improved global facial fine lines are attained according to the instant invention in a shorter time period than is typical with conventional home chemical peels (e.g., the peel moisturizer tested in the study as exemplified herein), and with less irritation than is observed with professional chemical peels. Longer term use of the inventive the skin-enhancing system, for example at least one month, confers enhanced reduction of fine lines and wrinkles, also with less irritation than is observed with professional chemical peels. In some embodiments, the chemical peel component is a home peel composition.

In accordance with the various embodiments, it is contemplated that some or all of following ingredients would be included in the compositions used according to the invention:

Oxidizing Component of the Skin-Enhancing Treatment

In various embodiments, the oxidizing component of the skin-enhancing system includes an oxidizing agent, for example, hydrogen peroxide. The oxidizing component of the skin-enhancing system also includes one or more additional ingredients, including water, at least one oil, at least one chelator, and may further include one or more ingredients selected from the group consisting of one or more water based solvents, one or more surfactants, one or more thickeners, and one or more additional ingredients selected from, but not limited to, pH adjusters, active components, humectants, antioxidants, plant extracts, plant oils and butters, fragrances, pearlescent agents, odor absorbers, coloring materials, essential oils, vitamins, antimicrobials and preservatives, and combinations of these.

The oxidizing component can be provided in a form that is rinse off or leave on. For example, the oxidizing component may be used in a creamy emulsion form, for example as a rinse-off mask, or a leave-on emulsion moisturizer or toner form, that may be thick or liquidous (flowable). Other formulations are possible, and the provided examples are non-limiting. More generally, the oxidizing component may be provided as one of a leave-on or a rinse-off type formulation and in a form selected from the group consisting of a suspension, an emulsion cream, serum, essence, gel, or toner, and may be packaged in a form such as a stick, spray, ointment, paste, foam, mousse, shaving cream, wipe, patch, strip, film-forming product, mask, and combinations thereof.

In some particular embodiments, the oxidizing component of the skin-enhancing system is a creamy emulsion form that may be thick or liquidous (flowable). According to some exemplary embodiments wherein the oxidizing component of the skin-enhancing system is a creamy emulsion form, the composition may include an oxidizing agent comprising hydrogen peroxide, one or a combination of chelating agents including tetrasodium glutamate diacetate, tetrasodium phosphate, one or a combination of phosphoric acid and sodium phosphate, a combination of surfactants including steareth-2 and steareth-20, one or more polymers including sclerotium gum, one or more vitamin actives, one or more preservatives, and water present in an amount from about 35% to about 75%, by weight, based on the weight of the oxidizing component.

In some particular embodiments, the oxidizing component of the skin-enhancing system is a liquidous toner form.

Accordingly, the various ingredients that may be present in the oxidizing component of the skin-enhancing system are provided herein below or further herein in the section described as other ingredients, and as shown in the Examples herein.

Oxidizing Agent

In some embodiments, the oxidizing component of the skin-enhancing system may comprise one or more of hydrogen peroxide, urea peroxide, carbamide peroxide, and PVP hydrogen peroxide (a complex of polyvinylpyrrolidone and hydrogen peroxide). In some particular embodiments, the oxidizing component of the skin-enhancing system comprises hydrogen peroxide.

In accordance with the various embodiments, amount of oxidizing agent present in the oxidizing component of the skin-enhancing system can range from about 1% to about 10%, from about 1% to about 7%, from about 1.0% to about 5%, from about 1.0% to about 4.0%, from 1.5% to about 4.5%, or about 4% or any suitable combination, sub-combination, range, or sub-range thereof by weight, based on the weight of the oxidizing component of the skin-enhancing system. One of ordinary skill in the art, however, will appreciate that other ranges are within the scope of the invention.

Thus, at least one oxidizing agent may be present, by weight, based on the weight of the oxidizing component of the skin-enhancing system, each present from about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, to about 10 weight percent, including increments and ranges therein and there between.

Oil

In accordance with the disclosure, one or more oil or oil is present in the oxidizing component of the skin-enhancing system. The oil includes one or more of non-silicone oils of animal, plant, mineral or synthetic origin, silicone oils, hydrocarbon compounds, fatty alcohols, fatty acids, esters of a fatty acid and/or of a fatty alcohol, non-silicone waxes, and silicones.

In some embodiments, the oil includes, but is not limited to: 1) C6-C16 lower alkanes, non-silicone oils of animal, plant, mineral or synthetic origin, fatty alcohols, fatty acids, non-silicone waxes, and silicones; 2) hydrocarbon-based oils of animal origin, such as perhydrosqualene (also known as "squalene"); 3) fluoro oils, perfluoromethycyclopentane and perfluoro-1,3-dimethylcyclohexane, sold under the name FLUTEC© PC1 and FLUTEC© PC3 by the company BNFL Fluorochemicals; perfluoro-1,2-dimethylcyclobutane; perfluoroalkanes such as dodecafluoropentane and tetradecafluorohexane, sold under the names PF 5050© by the company 3M, or bromoperfluorooctyl sold under the name FORALKYL© by the company Atochem; nonafluoromethoxybutane and nonafluoroethoxyisobutane; perfluoromorpholine derivatives such as 4-trifluoromethyl perfluoromorpholine sold under the same PF 5052© by the company 3M. 4) linear or branched saturated fatty alcohols having from 6 to 30 carbon atoms or from 8 to 30 carbon atoms, for instance cetyl alcohol, stearyl alcohol, and the mixture thereof (cetylstearyl alcohol), octyldodecanol, 2-butyloctanol, 2-hexyldecanol, 2-undecylpentadecanol, oleyl alcohol, and linoleyl alcohol.

In some embodiments, the at least one oil is an organic compound that is insoluble in water at ordinary ambient temperature (25° C.) and at atmospheric pressure (760 mmHg). In some embodiments, the at least one fatty substance has a water solubility of less than 5%. In some embodiments, the at least one oil has a water solubility of less than 1%. In some embodiments, the at least one fatty substance has a water solubility of less than 0.1%. Although these oils are given as an example, it will be appreciated that other compounds compatible with cosmetic applications known in the art may be used.

In some embodiments, a skin-brightening cosmetic composition comprises at least one oil selected from C6-C16 lower alkanes, non-silicone oils of animal, plant, mineral or synthetic origin alcohols, fatty acids, fatty acid esters and/or fatty alcohol esters, non-silicone waxes, silicones, and combinations thereof. In some embodiments, the at least one oil includes mineral oil, squalene, liquid petroleum jelly, polydecenes, silicone oil, liquid esters of fatty acids and/or of fatty alcohols, or combinations thereof. In some particular embodiments, the oil includes one or more of hemisqualane, dimethicone, squalane and combinations thereof.

In accordance with the various embodiments, amounts of the oils present in the oxidizing component of the skin-enhancing system can range from about 20% to about 80%, or from about 35 to about 60%, from about 40 to about 59%, from about 45 to about 58%, from about 50 to about 57%, from about 52 to about 56%, from about 30 to about 55%, from about 30 to about 60% or any suitable combination, sub-combination, range, or sub-range thereof by weight, based on the weight of the oxidizing component of the skin-enhancing system. In some embodiments, the oxidizing component of the skin-enhancing system includes at least about 2% of the oil. And, in some embodiments, the oxidizing component of the skin-enhancing system includes at least about 50% of the oil. Thus, in some embodiments, the oil is present in an amount that is not less than about 20%, or about 50%, based upon the total weight of the oxidizing component of the skin-enhancing system. One of ordinary skill in the art, however, will appreciate that other ranges are within the scope of the invention. In some embodiments, two or more oils are present. And, in some embodiments, one or more oils are present wherein at least one is an oxidation resistant oil.

Thus, any one of or a combination of oils may be present, by weight, based on the weight of the oxidizing component of the skin-enhancing system, each one or the combination present from about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, to about 80 weight percent, including increments and ranges therein and there between.

Solvent

In accordance with the disclosure, one or more solvent is present in the oxidizing component of the skin-enhancing system. The solvent present in the oxidizing component of the skin-enhancing system includes, but is not limited to, water, alcohol, propylene glycol, or combinations thereof. Although these solvents are given as an example, it will be appreciated that other solvents compatible with cosmetic applications known in the art may be used.

In accordance with the various embodiments, solvent is present in a given composition in an amount of from about 1% to about 70%, or any suitable combination, sub-combination, range, or sub-range thereof by weight, based on the weight of the oxidizing component of the skin-enhancing system. One of ordinary skill in the art, however, will appreciate that other ranges are within the scope of the invention.

Thus, one or a combination of solvents may be present, by weight, based on the weight of the oxidizing component of the skin-enhancing system, each one or the combination present from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, to about 70 weight percent, including increments and ranges therein and there between.

Water

The oxidizing component of the skin-enhancing systems comprise from about 1 to about 95% by weight of water, with respect to the total weight of the oxidizing component of the skin-enhancing system. In some embodiments, the amount of water in the oxidizing component of the skin-enhancing system can range from about 1 to about 70%, or any suitable combination, sub-combination, range, or sub-range thereof by weight, based on the weight of the oxidizing component of the skin-enhancing system.

The pH of the oxidizing component of the skin-enhancing system is not limited but is generally between 3 and 10, and in some embodiments is one of between 3 and 11, and between 5 and 9, and between 6 and 8, and 7. The pH can be adjusted to the desired value by addition of a base (organic or inorganic) to the oxidizing component of the skin-enhancing system, for example ammonia or a primary, secondary or tertiary (poly)amine, such as monoethanolamine, diethanolamine, triethanolamine, isopropanolamine or 1,3-propanediamine, or sodium phosphate, phosphoric acid, citric acid, sodium hydroxide, or combinations thereof. Accordingly, in some embodiments of the skin-enhancing system wherein the pH is between 3-5, inorganic acid, for example, phosphoric acid, is added to adjust the pH, and in other embodiments, wherein the pH is between 5~10, a second pH adjusting composition with a basic pH will can be mixed with the oxidizing component prior to application to achieve a higher pH.

Thus, water may be present by weight, based on the weight of the oxidizing component of the skin-enhancing system, from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90 to about 95 weight percent, including increments and ranges therein and there between.

Surfactant

In some embodiments, the oxidizing component of the skin-enhancing system may include at least one surfactant. The at least one surfactant may be selected from nonionic surfactants and anionic surfactants. In some embodiments, the oxidizing component of the skin-enhancing system includes one, two, three or more surfactants. In some exemplary embodiments, the surfactant or surfactants are nonionic. In some embodiments, the at least one surfactant includes monoxyalkylenated or polyoxyalkylenated nonionic surfactants, monoglycerolated or polyglycerolated nonionic surfactants, alkylpolyglucoside nonionic surfactants, or combinations thereof. In some embodiments, the oxidizing component of the skin-enhancing system includes at least one nonionic surfactant. In some embodiments, the oxidizing component of the skin-enhancing system includes two or more surfactants, and in some such embodiments, at least one surfactant has a low HLB (about 5) and at least one surfactant has a high HLB (about 15).

Exemplary anionic surfactants include, but are not limited to, the salts (in particular alkali metal salts, for example, sodium salts, amine salts such as aminoalcohol salts or alkaline-earth metal salts such as magnesium salts) of the following compounds: alkyl sulfates, alkyl ether sulfates, alkylamido ether sulfates, alkylaryl polyether sulfates, monoglyceride sulfates; alkylsulfonates, alkylamidesulfonates, alkylarylsulfonates, α-olefin sulfonates, paraffin sulfonates; alkyl phosphates, alkyl ether phosphates; alkylsulfosuccinates, alkyl ether sulfosuccinates, alkylamidesulfosuccinates; alkylsulfosuccinamates; alkylsulfoacetates; acylsarcosinates; acylisethionates and N-acyltaurates; salts of fatty acids such as oleic acid, ricinoleic acid, palmitic acid or stearic acid, coconut oil acid or hydrogenated coconut oil acid; alkyl-D-galactoside uronic acid salts; acyllactylates; salts of polyoxyalkylenated alkyl ether carboxylic acids, of polyoxyalkylenated alkylaryl ether carboxylic acids or of polyoxyalkylenated alkylamido ether carboxylic acids, in particular those having from 2 to 50 ethylene oxide groups; and combinations thereof.

Exemplary nonionic surfactants include, but are not limited to, monooxyalkylenated or polyoxyalkylenated nonionic surfactants, monoglycerolated or polyglycerolated nonionic surfactants, or alkylpolyglucosides. The oxyalkylene units may be oxyethylene or oxypropylene units, or a combination thereof. In some embodiments, the oxyalkylene units are oxyethylene units. Exemplary oxyalkylenated nonionic surfactants include, but are not limited to: oxyalkylenated (C8-C24)alkylphenols, saturated or unsaturated, linear or branched, oxyalkylenated C8-C30 alcohols, saturated or unsaturated, linear or branched, oxyalkylenated C8-C30 amides, esters of saturated or unsaturated, linear or branched, C8-C30 acids and of polyethylene glycols, polyoxyethylenated esters of saturated or unsaturated, linear or branched, C8-C30 acids and of sorbitol, saturated or unsaturated, oxyethylenated plant oils, condensates of ethylene oxide and/or of propylene oxide, inter alia, alone or as a mixture. Exemplary alkylpolyglucosides include, but are not limited to, decyl glucoside, caprylyl/capryl glucoside, laurylglucoside, coco-glucoside, cetostearyl glucoside possibly mixed with cetostearyl alcohol, arachidyl glucoside, cocoylethylglucoside, and combinations thereof.

In some embodiments, the at least one surfactant present in the oxidizing component of the skin-enhancing system is a nonionic surfactant. In some exemplary embodiments, one or more surfactants in the oxidizing component of the skin-enhancing system are selected from oxyalkylenated (C8-C24) alkylphenols, saturated or unsaturated, linear or branched, oxyalkylenated C8-C30 alcohols, saturated or unsaturated, linear or branched, oxyalkylenated C8-C30 amides, esters of saturated or unsaturated, linear or branched, C8-C30 acids and of polyethylene glycols, polyoxyethylenated esters of saturated or unsaturated, linear or branched, C8-C30 acids and of sorbitol, saturated or unsaturated, oxyethylenated plant oils, condensates of ethylene oxide and/or propylene oxide and combinations thereof. In some exemplary embodiments a composition includes two or more of non-ionic surfactants selected from oxyethylenated C8-C30 alcohols, polyoxyethylenated linear or branched, saturated or unsaturated C8-C30 acid esters, and polyoxyethylenated sorbitol esters.

In some embodiments, the oxidizing component of the skin-enhancing system includes two or more surfactants, and in some such embodiments, at least one surfactant has a low HLB (about 5), and in the range from about 1-8, more preferably 3≤HLB≤8, and at least one surfactant has a high HLB (about 15) and in the range from about 8-25, more preferably 10≤HLB≤16. In accordance with such embodiments, at least one surfactant has an HLB in the range from about 1 to about 8, for example from about 1, 2, 3, 4, 5, 6, 7, or 8, and at least one surfactant has an HLB in the range from about 8 to about 25, for example, from about 8, 9, 10, 11, 12, 13, 14, 15, 16, 17, 18, 19, 20, 21, 22, 23, 24 or 25. In some exemplary embodiments, a composition includes one or more of ceteth-2 (HLB ~5) and steareth-2 (HLB ~5), and one or more of decyl glucoside (HLB ~13-15) and steareth-20 (HLB ~15).

In some embodiments, the at least one surfactant is present in the oxidizing component of the skin-enhancing system in an amount ranging from about 0.1% to about 15% by weight relative to the weight of the oxidizing component of the skin-enhancing system. In some embodiments, the at least one surfactant is present in the oxidizing component of the skin-enhancing system in an amount ranging from about 0.5% to about 3.5% by weight, including increments and ranges therein and there between, based upon the total weight of the oxidizing component of the skin-enhancing system.

In some embodiments, one or more surfactants, alone or in combination, can be present in the oxidizing component of the skin-enhancing system, and in some embodiments, each surfactant may be present from about 0.1% to about 5% by weight, from about 0.25% to about 2.5% by weight, from about 0.5% to about 1.8%, from about 0.5 to about 1.25%, and from about 0.5 to about 0.8%, or any suitable combination, sub-combination, range, or sub-range thereof by weight, based on the weight of the oxidizing component of the skin-enhancing system.

It will be appreciated that in some embodiments, the skin-enhancing system is free or essentially free of surfactant. In some embodiments, at least the oxidizing component of the skin-enhancing system is free or essentially free of surfactant.

Thus, one or a combination of surfactants, if present, may be present, by weight, based on the weight of the oxidizing component of the skin-enhancing system, each one or the combination present from about 0.1, 0.2, 0.3, 0.4, 0.5, 0.6, 0.7, 0.8, 0.9, 1.0, 2, 3, 4, 5, 6, 7, 8, 9, 10, 11, 12, 13, 14, to about 15 weight percent, including increments and ranges therein and there between.

Polymer

In some embodiments, one or more other components, such as polymers can be present in the oxidizing component of the skin-enhancing system from about 0.05% to about 50% by weight, from about 0.05% to about 15% by weight, from about 0.1 to about 2%, from about 0.25 to about 1.5%, and from about 0.25 to about 0.5%, or any suitable combination, sub-combination, range, or sub-range thereof by weight, based on the weight of the oxidizing component of the skin-enhancing system. One of ordinary skill in the art, however, will appreciate that other ranges are within the scope of the invention. In some embodiments, polymers are selected from fatty acid amides, cellulose-based thickeners, guar gum and derivatives, gum of microbial origin, carrageenan, crosslinked homopolymers of acrylic acid or of acrylamidopropanesulfonic acid and associative polymers. In some exemplary embodiments, polymers are selected from cetyl hydroxyethylcellulose, sclerotium gum at 1% or more by weight, and combinations of these.

Thus, one or a combination of polymers may be present, by weight, based on the weight of the oxidizing component of the skin-enhancing system, each one or the combination present from about 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 weight percent, including increments and ranges therein and there between.

Chemical Peel Component of the Skin-Enhancing Treatment

In various embodiments, the chemical peel component of the skin-enhancing system includes at least one or a combination of alpha hydroxy acids and at least one or a combination of beta hydroxy acids. In some embodiments, the chemical peel component of the skin-enhancing system includes at least one alpha hydroxy acid comprising lactic acid and at least one beta hydroxy acid comprising salicylic acid. The chemical peel component of the skin-enhancing system also includes one or more additional ingredients, including water, and one or more ingredients selected from the group consisting of one or more oils, one or more water based solvents, one or more surfactants, one or more thickeners, phenylethyl resorcinol, and one or more additional ingredients selected from, but not limited to, chelating agents, pH adjusters, active components, humectants, antioxidants, plant extracts, plant oils and butters, fragrances, pearlescent agents, odor absorbers, coloring materials, essential oils, vitamins, antimicrobials and preservatives, and combinations of these.

In some particular embodiments, the chemical peel component of the skin-enhancing system is a creamy emulsion form that may be thick or liquidous (flowable). In some particular embodiments, the chemical peel component of the skin-enhancing system is a liquidous toner form. The chemical peel component can be provided in a form that is rinse off or leave on. For example, the chemical peel component may be used in a creamy emulsion form, for example as a rinse-off mask, or a leave-on toner form. Other formulations are possible, and the provided examples are non-limiting. More generally, the chemical peel component may be provided as one of a leave-on or a rinse-off type formulation and in a form selected from the group consisting of a suspension, an emulsion cream, serum, essence, gel, or toner, and may be packaged in a form such as a stick, spray, ointment, paste, foam, mousse, shaving cream, wipe, patch, strip, film-forming product, mask, and combinations thereof.

In some particular embodiments, the chemical peel component of the skin-enhancing system is a creamy emulsion form that may be thick or liquidous (flowable). According to some exemplary embodiments wherein the chemical peel of the skin-enhancing system is a creamy emulsion form, the composition may include at least one alpha hydroxy acid comprising lactic acid and at least one beta hydroxy acid comprising salicylic acid, one or a combination of oils or plant butters, one or a combination of surfactants, one or more thickeners, one or more water based solvents, for example, glycerin, one or more vitamin actives, one or more preservatives, chelating agents, or pH adjusters, and water present in an amount from about 40% to about 50%, by weight, based on the weight of the skin peel component.

In some particular embodiments, the chemical peel component of the skin-enhancing system is a toner, wherein the composition may include at least one alpha hydroxy acid comprising lactic acid and at least one beta hydroxy acid comprising salicylic acid, one or a combination of oils including squalane and nut oils, one or a combination of surfactants including betaine, one or more thickeners including carrageenan, one or more water based solvents, for example, glycerin or propanediol, one or more actives including hyaluronic acid, one or more fragrances, preservatives, chelating agents, or pH adjusters, and water present in an amount from about 70% to about 75%, by weight, based on the weight of the skin peel component. And in some particular embodiments, the chemical peel component of the skin-enhancing system is a toner, wherein the composition may include at least one alpha hydroxy acid comprising lactic acid and at least one beta hydroxy acid comprising salicylic acid, phenylethyl resorcinol, one or a combination of water based solvents including denatured alcohol, one or more, preservatives, chelating agents, or pH adjusters, and water present in an amount from about 70% to about 75%, by weight, based on the weight of the skin peel component.

Accordingly, the various ingredients that may be present in the chemical peel component of the skin-enhancing system are provided herein below or further herein in the section described as other ingredients, and as shown in the Examples herein.

Alpha Hydroxy Acid

In accordance with the various embodiments, the chemical peel component of the skin-enhancing system comprises at least one alpha hydroxy acid.

Suitable alpha hydroxy acids include glycolic acid, lactic acid, tartaric acid, mandelic acid, citric acid, ester derivatives thereof and combinations thereof. Exemplary ester derivatives include ester compounds of lactic acid, such as methyl lactate, ethyl lactate, butyl lactate and, similarly, ester compounds of glycolic acid, tartaric acid, mandelic acid, citric acid. One particularly suitable alpha hydroxy acid is lactic acid. Lactic acid, or 2-hydroxypropanoic acid, is provided to the chemical peel composition to provide enhanced exfoliation of the skin. In addition, lactic acid also boosts production of glycosaminoglycan (GAG) in the skin, improving the barrier function and moisturization of skin.

And in some particular embodiments, the alpha hydroxy acid in the chemical peel component of the skin-enhancing system excludes at least one of lactic acid, glycolic acid, tartaric acid, mandelic acid, and citric acid.

The chemical peel component of the skin-enhancing system includes a concentration of alpha hydroxy acid in a range from about 4% to about 15%, or from about 8% to about 14% or from about 9% to about 13%, or from about 10% to about 12%, or is about 10%, or any suitable combination, sub-combination, range, or sub-range thereof by weight, based on the weight of the chemical peel component of the skin-enhancing system. One of ordinary skill in the art, however, will appreciate that other ranges are within the scope of the invention. In accordance with some embodiments, the amount of alpha hydroxy acid present is not more than about 10%.

Thus, any one of or a combination of alpha hydroxy acid is present, by weight, based on the total weight of the chemical peel component of the skin-enhancing system, from about 4, 5, 6, 7, 8, 9, 10, 11, 12, 13, 14, to about 15 weight percent, including increments and ranges therein and there between.

Beta Hydroxy Acid

In accordance with the various embodiments, the chemical peel component of the skin-enhancing system may comprise at least one beta hydroxy acid. In some particular embodiments, the chemical peel component of the skin-enhancing system may include a beta hydroxy acid comprising salicylic acid.

The term "beta-hydroxy acid" is understood to mean, according to the present invention, a carboxylic acid having a hydroxyl functional group and a carboxylic functional group separated by two carbon atoms. A beta hydroxy acid can be present in the chemical peel component of the skin-enhancing system in the form of the free acid and/or in the form of one of its associated salts (salts with an organic base or an alkali metal, in particular), especially according to the final pH imposed on the chemical peel component of the skin-enhancing system.

Suitable beta hydroxy acids include salicylic acid and derivatives thereof (including 5-n-octanoylsalicylic acid, salicylate, sodium salicylate, and willow extract), capryloyl salicylic acid, beta hydroxybutanoic acid, propionic acid, beta-hydroxy beata-methylbutyric acid, carnitine tropic acid, and trethocanic acid, and combinations of these.

And in some particular embodiments, the beta hydroxy acid in the chemical peel component of the skin-enhancing system excludes at least one of salicylic acid and derivatives thereof (including 5-n-octanoylsalicylic acid, salicylate, sodium salicylate, and willow extract), capryloyl salicylic acid, beta hydroxybutanoic acid, propionic acid, beta-hydroxy beata-methylbutyric acid, carnitine tropic acid, and trethocanic acid.

The chemical peel component of the skin-enhancing system may include a concentration of beta hydroxy acid in a range from about 0.1% up to and not more than about 2% of beta hydroxy acid, by weight, based on the total weight of the chemical peel component of the skin-enhancing system. In some embodiments, the chemical peel component of the skin-enhancing system includes up to and not more than about 2%, or about 1.9% of beta hydroxy acid. In some embodiments, the chemical peel component of the skin-enhancing system includes up to and not more than about 1% of beta hydroxy acid. In accordance with some embodiments, the amount of beta hydroxy acid present is not more than about 0.40% to about 0.50%. In some embodiments, the chemical peel component of the skin-enhancing system includes from about 0.1% to about 1% of beta hydroxy acid, or from about 0.2% to about 2.0%, or from about 0.1% to about 1.5%, or from about 0.2% to about 1.5%, or from about 0.3% to about 1.0%, or from about 0.35% to about 0.75%, or from about 0.4% to about 0.5%, or is about 0.45%, or any suitable combination, sub-combination, range, or sub-range thereof by weight, based on the weight of the chemical peel component of the skin-enhancing system. One of ordinary skill in the art, however, will appreciate that other ranges are within the scope of the invention.

Thus, the at least one beta hydroxy acid, when present, is present in the chemical peel component of the skin-enhancing system from about 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, to about 2.0 weight percent, including increments and all ranges and subranges therein and there between.

Poly Hydroxy Acid

In accordance with the various embodiments, the chemical peel component of the skin-enhancing system may comprise at least one poly hydroxy acid.

Suitable poly hydroxy acids include gluconolactone and derivatives thereof and combinations thereof.

The chemical peel component of the skin-enhancing system may include a concentration of poly hydroxy acid in a range from about 4% to about 15%, or from about 8% to about 14% or from about 9% to about 13%, or from about 10% to about 12%, or is about 10%, or any suitable combination, sub-combination, range, or sub-range thereof by weight, based on the weight of the chemical peel component of the skin-enhancing system. One of ordinary skill in the art, however, will appreciate that other ranges are within the scope of the invention. In accordance with some embodiments, the amount of poly hydroxy acid present is not more than about 10%.

Thus, any one of or a combination of poly hydroxy acid, when present, is present, by weight, based on the total weight of the chemical peel component of the skin-enhancing system, from about 4, 5, 6, 7, 8, 9, 10, 11, 12, 13, 14, to about 15 weight percent, including increments and ranges therein and there between.

Phenylethyl Resorcinol

In accordance with some embodiments, the chemical peel component of the skin-enhancing system may comprise phenylethyl resorcinol.

Phenylethyl resorcinol functions a tyrosinase inhibitor. The phenylethyl resorcinol, when utilized in the chemical peel component of the skin-enhancing system effectively whiten skin and reduce skin tone unevenness. Phenylethyl resorcinol has not shown adverse effects in basic toxicological tests, including acute oral toxicity, mutagenicity, skin irritation, skin sensitization, and phototoxicity.

In accordance with the various embodiments, when present, the amount of phenylethyl resorcinol present in the chemical peel component of the skin-enhancing system is from about 0.2% to about 2.0%, or from about 0.2% to about 1.5%, or from about 0.4% to about 1.0%, or from about 0.6% to about 0.9%, or from about 0.7% to about 0.8%, or from about 0.2% to about 0.8%, is about 0.75%, or any suitable combination, sub-combination, range, or sub-range thereof by weight, based on the weight of the chemical peel component of the skin-enhancing system. One of ordinary skill in the art, however, will appreciate that other ranges are within the scope of the invention. In accordance with some embodiments, the amount of phenylethyl resorcinol present is not more than about 0.2% to about 0.8%.

Thus, phenylethyl resorcinol, when present in the chemical peel component of the skin-enhancing system, is present, by weight, based on the total weight of the chemical peel component of the skin-enhancing system, from about 0.20, 0.30, 0.40, 0.50, 0.60, 0.70, 0.80, 0.90, 1.0, 1.1, 1.2, 1.3, 1.4, 1.5, 1.6, 1.7, 1.8, 1.9 to about 2.0 weight percent, including increments and ranges therein and there between.

Oil

In accordance with the various embodiments, the chemical peel component of the skin-enhancing system may include one or more non water-immiscible oils.

In some particular embodiments, the chemical peel component in an emulsion form may include one or more oils selected from the group consisting of C12-15 alkyl benzoate, caprylic/capric triglyceride, *Theobroma cacao* (cocoa) seed butter, *butyrospermum parkii* (shea) butter, coco-caprylate/caprate, and combinations thereof.

In the various embodiments, some particular embodiments, the chemical peel component in an emulsion form includes at least one lightweight emollient selected from polar emollients and linear liquid alkanes. In some particular embodiments, the composition comprises one or a combination of coco-caprylate/caprate or C15-19 alkane.

The at least one lightweight emollient is present in a range from about 0.5% to about 15%, or from about 1% to about 12%, or from about 1% to about 10%, or from about 2% to about 8%, or any suitable combination, sub-combination, range, or sub-range thereof by weight, based on the weight of the chemical peel component. One of ordinary skill in the art, however, will appreciate that other ranges are within the scope of the invention.

Other suitable polar emollients may be selected from the group consisting of Isopropyl myristate, dicaprylyl ether, ethylhexyl palmitate, Isopropyl palmitate, cetearyl ethylhexanoate, Isononyl isononanoate, isopropyl isostearate, diisopropyl sebacate, coco caprylate/caprate, diisopropyl adipate, and combinations thereof.

Other suitable linear liquid alkanes (C11 to C20) may be selected from the group consisting of isohexadecane, C15-19 alkane, isododecane, undecane, tridecane, dodecane, and combinations thereof.

In some particular embodiments, the chemical peel component includes coco-caprylate/caprate, C15-19 alkane, dodecane and combinations thereof.

Thus, any one of or a combination of lightweight emollient is present, by weight, based on the total weight of the chemical peel component, from about 0.5, 0.6, 0.7, 0.8, 0.9, 1, 2, 3, 4, 5, 6, 7, 8, 9, 10, 11, 12, 13, 14, to about 15 weight percent, including increments and ranges therein and there between.

In some particular embodiments, the chemical peel component in a toner form may include one or more oils selected from the group consisting of dicaprylyl ether, *macadamia ternifolia* seed oil, squalane, and combinations thereof.

In the various embodiments, the oil is generally immiscible in water, and may be selected from hydrocarbons, silicones, fatty alcohols, glycols and vegetable oils. The oil may include one or a combination of polar and non-polar oil. In some embodiments, the oil may be chosen from hydrocarbon-based oils from plants or of plant origin, mineral oil, ester oils, fatty alcohols containing from 12 to 26 carbon atoms, fatty acids containing from 12 to 26 carbon atoms and vinylpyrrolidone copolymers, and combinations thereof. In some particular embodiments, an oil may be chosen from purcellin oil (cetostearyl octanoate), squalane, hemisqualane, isononyl isononanoate, C12 to C15 alkyl benzoate, 2-ethylhexyl palmitate, isodecyl neopentanoate, tridecyl neopentanoate, octyldodecyl neopentanoate, 2-octyldodecyl stearate, 2-octyldodecyl erucate, oleyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate and 2-diethylhexyl succinate, cocoglyceride, cyclomethicone, dimethicone, dicaprylyl carbonate, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid, oleic acid, stearic acid, fatty alcohol, cetyl alcohol, hexadecyl alcohol, diisopropyl adipate, hydroxybenzoate esters, benzoic acid esters of C9-C15 alcohols, alkanes, mineral oil, silicone, dimethyl polysiloxane, ether, polyoxypropylene butyl ether, polyoxypropylene cetyl ether, C12-C15 alkyl benzoate, aryl alkyl benzoate, Isopropyl Lauroyl sarcosinate, and any combinations thereof.

In some particular embodiments, the oil is chosen from C13-15 alkane (hemisqualane), dicaprylyl carbonate, isononyl isononanoate, isopropyl myristate, dimethicone, squalane, and mineral oil. In an exemplary embodiment, the oil comprises one or a combination of C13-15 alkane (hemisqualane), dicaprylyl carbonate, isononyl isononanoate, isopropyl myristate, dimethicone, squalane, and mineral oil. In some embodiments, the oil in the chemical peel component of the skin-enhancing system includes isopropyl myristate.

In accordance with the various embodiments, additional oil, when present, in the chemical peel component is at present from about 1% to about 20%. One of ordinary skill in the art, however, will appreciate that other ranges are within the scope of the invention. The chemical peel component may include more than one oil, such as a mixture of oils wherein one or the mixture of oils is present in an amount that alone or combined is present from about 1% to about 20% by weight based on the weight of the chemical peel component, and wherein the total amount of additional oil is present up to about 20% of the chemical peel component.

In accordance with some embodiments, the chemical peel component may comprise at least one plant butter, the at least one butter selected from the group consisting of *butyrospermum parkii* (shea) butter, *Theobroma cacao* (cocoa) seed butter, almond butter, aloe butter, apricot kernel butter, avocado butter, coconut cream butter, cupuacu butter, dhupu butter, hemp butter, jojoba butter, kokum butter, *macadamia* nut butter, mango butter and combinations thereof.

In accordance with the various embodiments, the amount of butter present in the chemical peel component may be at least 1%, alternatively from about 1% to about 10%; alternatively, from about 2% to about 9%, alternatively from about 3% to about 8%, alternatively from about 4% to about 7%, alternatively from about 5% to about 6%, or any suitable combination, sub-combination, range, or sub-range thereof by weight, based on the weight of the chemical peel component. One of ordinary skill in the art, however, will appreciate that other ranges are within the scope of the invention.

In some embodiments, the at least one butter has a melting point in the range of from about 30 to about 45 degrees Celsius.

Thus, any one of or a combination of oils may be present, by weight, based on the total weight of the chemical peel component, from about 1, 2, 3, 4, 5, 6, 7, 8, 9, 10, 11, 12, 13, 14, 15, 16, 17, 18, 19, to about 20 weight percent, including increments and ranges therein and there between.

In some embodiments, when present, the amount of at least one oil present in the chemical peel component of the skin-enhancing system may be at least about 20%, and can range from about 20% to about 60%, or from about 25% to about 55%, or from about 30% to about 50%, or any suitable combination, sub-combination, range, or sub-range thereof by weight, based on the weight of the chemical peel component of the skin-enhancing system. One of ordinary skill in the art, however, will appreciate that other ranges are within the scope of the invention. The chemical peel component of the skin-enhancing system may include more than one oil, such as a mixture of oils wherein one or the mixture of oils is present in an amount that alone or combined is at least 20% by weight based on the weight of the chemical peel component of the skin-enhancing system, and wherein the total amount of oil is present up to about 60% of the chemical peel component of the skin-enhancing system.

Thus, any one of or a combination of oils may be present, by weight, based on the total weight of the chemical peel component of the skin-enhancing system, from about at least 20, 21, 22, 23, 24, 25, 26, 27, 28, 29, 31, 31, 32, 33, 34, 35, 36, 37, 38, 39, 40, 41, 42, 43, 44, 45, 46, 47, 48, 49, 50, 51, 52, 53, 54, 55, 56, 57, 58, 59 to about 60 weight percent, including increments and ranges therein and there between.
Solvent In accordance with the various embodiments, water is present in the chemical peel component of the skin-enhancing system in a range from about 20% to about 80%, or from about 30% to about 60%, or from about 35% to about 50%, or from about 45% to about 49%, or from about 60% to about 80%, or from about 65% to about 75%, or any suitable combination, sub-combination, range, or sub-range thereof by weight, based on the weight of the chemical peel component of the skin-enhancing system. One of ordinary skill in the art, however, will appreciate that other ranges are within the scope of the invention.

In some particular embodiments, wherein the chemical peel component is an emulsion form, water is present in the chemical peel component of the skin-enhancing system in a range from about 20% to about 80%, or from about 30% to about 60%, or from about 35% to about 50%, or from about 45% to about 49%%, or any suitable combination, sub-combination, range, or sub-range thereof by weight, based on the weight of the chemical peel component of the skin-enhancing system.

In some particular embodiments, wherein the chemical peel component is a toner form, water is present in the chemical peel component of the skin-enhancing system in a range from about 20% to about 80%, or from about 60% to about 80%, or from about 65% to about 75%%, or any suitable combination, sub-combination, range, or sub-range thereof by weight, based on the weight of the chemical peel component of the skin-enhancing system. One of ordinary skill in the art, however, will appreciate that other ranges are within the scope of the invention.

Thus, water is present, by weight, based on the total weight of the chemical peel component of the skin-enhancing system, from about 20, 21, 22, 23, 24, 25, 26, 27, 28, 29, 31, 31, 32, 33, 34, 35, 36, 37, 38, 39, 40, 41, 42, 43, 44, 45, 46, 47, 48, 49, 50, 51, 52, 53, 54, 55, 56, 57, 58, 59 to about 60 weight percent, including increments and ranges therein and there between.

In some embodiments, water is present in the chemical peel component in a range from about 40% to about 60%, or from about 45% to about 55%, or from about 48% to about 50%, or any suitable combination, sub-combination, range, or sub-range thereof by weight, based on the weight of the chemical peel component. One of ordinary skill in the art, however, will appreciate that other ranges are within the scope of the invention.

Thus, in some embodiments, water is present, by weight, based on the total weight of the chemical peel component, from about 40, 41, 42, 43, 44, 45, 46, 47, 48, 49, 50, 51, 52, 53, 54, 55, 56, 57, 58, 59 to about 60 weight percent, including increments and ranges therein and there between.

The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the chemical peel component of the skin-enhancing system is not limited but is generally not less than 3. In some embodiments, the pH of the chemical peel component is not limited but is generally not less than 3, and more particularly in a range from about 3 to about 4.5, or from about 3.5 to about 4.1, or about 3.8. The pH can be adjusted to the desired value by addition of a base (organic or inorganic) to the chemical peel component, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

In some embodiments, the chemical peel component includes one or more water based solvents selected from the group consisting of glycols, for example, glycerin and pentylene glycol, alcohols for solubilizing acid, for example, monoalcohols such as monohydric $C_1$-$C_8$ alcohols such as ethanol, propanol, butanol, isopropanol, isobutanol, and benzyl alcohol, and phenylethyl alcohol, and combinations thereof. In some embodiments, the water based solvents include glycerin and pentylene glycol. In some embodiments, glycerin is present in a range from about 5% to about 20%.

In accordance with the various embodiments, the amount of water based solvent present in the chemical peel component is in the range from about 1% to about 20%, or from about 2% to about 18%, or from about 10% to about 15%, or any suitable combination, sub-combination, range, or sub-range thereof by weight, based on the weight of the chemical peel component. One of ordinary skill in the art, however, will appreciate that other ranges are within the scope of the invention.

Thus, any one of or a combination of water based solvents may be present, by weight, based on the total weight of the chemical peel component, from about 1, 2, 3, 4, 5, 6, 7, 8, 9, 10, 11, 12, 13, 14, 15, 16, 17, 18, 19, to about 20 weight percent, including increments and ranges therein and there between.

In some embodiments, the chemical peel component of the skin-enhancing system includes one or more solvents comprising alcohol for solubilizing acid, for example, monoalcohols such as monohydric $C_1$-$C_8$ alcohols such as ethanol, propanol, butanol, isopropanol, isobutanol, and benzyl alcohol, and phenylethyl alcohol. In some embodiments, the alcohol solvent is selected from one or a combination of ethanol and isopropyl alcohol.

In accordance with the various embodiments, the amount of alcohol present in the chemical peel component of the skin-enhancing system is in the range from about 5% to about 20%, or from about 6% to about 18%, or from about 10% to about 15%, or any suitable combination, sub-combination, range, or sub-range thereof by weight, based on the weight of the chemical peel component of the skin-enhancing system. One of ordinary skill in the art, however, will appreciate that other ranges are within the scope of the invention.

Thus, any one of or a combination of alcohols may be present, by weight, based on the total weight of the chemical peel component of the skin-enhancing system, from about 5, 6, 7, 8, 9, 10, 11, 12, 13, 14, 15, 16, 17, 18, 19, to about 20 weight percent, including increments and ranges therein and there between.

Surfactant

In accordance with the disclosure, the chemical peel component of the skin-enhancing system includes one or more surfactants.

In accordance with some particular embodiments, the chemical peel component includes a blend of surfactants comprising one or a combination of surfactants, for example selected from the group consisting of stearic acid, polysorbate 20, glyceryl stearate (and) peg-100 stearate, cetearyl alcohol (and) ceteareth-20, and glyceryl stearate, sorbitan stearate, and combinations thereof.

In accordance with some particular embodiments, the chemical peel component includes a blend of surfactants comprising at least stearic acid, polysorbate 20, glyceryl stearate (and) peg-100 stearate, cetearyl alcohol (and) ceteareth-20, and glyceryl stearate.

In accordance with such embodiments, the amount of surfactant present in the composition may be from about 1% to about 20%, alternatively from about 2% to about 19%, alternatively from about 3% to about 18%, alternatively from about 4% to about 17%, alternatively from about 5% to about 16%, alternatively from about 6% to about 15%, alternatively from about 7% to about 14%, alternatively from about 8% to about 13%, alternatively from about 9% to about 12%, alternatively from about 10% to about 11%, or any suitable combination, sub-combination, range, or sub-range thereof by weight, based on the weight of the composition. One of ordinary skill in the art, however, will appreciate that other ranges are within the scope of the invention.

In some embodiments, surfactants selected are sulfate free. In some particular embodiments, the blend of surfactants comprises two or more surfactants that are sulfate-free. The term "sulfate-free" as used herein means that sulfate has not been added as a component. In some embodiments, a composition is devoid of sulfate. Those of skill in the art will appreciate that sulfate may be present in a composition via its presence in one or more of the formulation components; thus, in some embodiments a composition may be "essentially sulfate-free" wherein sulfate is present at a concentration that does not exceed 5% by weight, and in some instances is present not more than 3% by weight, and in some instances is present not more than 1% by weight, based on the weight of the cleansing composition. Thus, the term "sulfate-free" means that the surfactant does not include sulfate.

In accordance with such embodiments, each one of the surfactants in the blend of surfactants is present in the composition in an amount from about 0.5% to about 8%, or from about 1% to about 4%, or any suitable combination, sub-combination, range, or sub-range thereof by weight, based on the weight of the moisturizing peel cream. In some embodiments, a blend of surfactants is present in the composition in an amount from about 5% to about 8%, or any suitable combination, sub-combination, range, or sub-range thereof by weight, based on the weight of the moisturizing peel cream. One of ordinary skill in the art, however, will appreciate that other ranges are within the scope of the invention.

Thus, each one of the surfactants, in particular when selected from stearic acid, polysorbate 20, glyceryl stearate (and) peg-100 stearate, cetearyl alcohol (and) ceteareth-20, and glyceryl stearate, alone or in combination, is present in an amount by weight, based on the total weight of the moisturizing peel cream, from about 0.5, 0.6, 0.7, 0.8, 0.9, 1, 2, 3, 4, 5, 6, 7, to about 8 weight percent, including increments and ranges therein and there between.

In some embodiments, surfactants are selected from anionic surfactants, amphoteric/zwitterionic surfactants, and non-ionic surfactants. In accordance with some embodiments, the chemical peel component of the skin-enhancing system comprises one surfactant, or a blend of surfactants that comprises two or more surfactants selected from anionic surfactants, amphoteric/zwitterionic surfactants, non-ionic surfactants, and combinations thereof. In some such embodiments, the blend of two or more surfactants comprises surfactants that are selected from only one of anionic surfactants, amphoteric/zwitterionic surfactants, non-ionic surfactants. In some embodiments, the blend of two or more surfactants comprises surfactants that are selected from at least two of anionic surfactants, amphoteric/zwitterionic surfactants, non-ionic surfactants. In some embodiments, the blend of surfactants comprises only two surfactants. In some embodiments, the blend of surfactants comprises three or more surfactants.

In some embodiments, anionic surfactants may be selected from, for example, alkyl sulfonates, alkyl sulfosuccinates, alkyl ether sulfosuccinates, alkyl sulfoacetates, alkyl sulfosuccinamates, alkyl ether carboxylates, alkyl succinates, fatty acyl taurates, fatty acyl isethionates, fatty acyl sarcosinates, fatty acyl glutamates, fatty acyl glycinates, and alkyl phosphates.

In some embodiments, amphoteric/zwitterionic surfactants may be selected from, for example, amphocarboxylates, alkyl betaines, amidoalkyl betaines, amphophosphates, phosphobetaines, pyrophosphobetaines, carboxyalkyl polyamines, and amidoalkyl sultaines.

In some embodiments, non-ionic surfactants may be selected from, for example, alkyl polyglucosides having alkyl groups with carbon chain length from C10 to C16.

In some embodiments, surfactants selected are sulfate free. In some particular embodiments, the blend of surfactants comprises two or more surfactants that are sulfate-free. The term "sulfate-free" as used herein means that sulfate has not been added as a component. In some embodiments, a composition is devoid of sulfate. Those of skill in the art will appreciate that sulfate may be present in a composition via its presence in one or more of the formulation components; thus, in some embodiments a composition may be "essentially sulfate-free" wherein sulfate is present at a concentration that does not exceed 5% by weight, and in some instances is present not more than 3% by weight, and in some instances is present not more than 1% by weight, based on the weight of the cleansing composition. Thus, the term "sulfate-free" means that the surfactant does not include sulfate.

In accordance with the various embodiments, each one of the surfactants in the blend of surfactants is present in the composition in an amount from about 2% to about 12%, or from about 3% to about 4%, or any suitable combination, sub-combination, range, or sub-range thereof by weight, based on the weight of the chemical peel component of the skin-enhancing system. In some embodiments, a blend of surfactants is present in the composition in an amount from about 4% to about 25%, or from about 6% to about 12%, or from about 6% to about 8% or any suitable combination, sub-combination, range, or sub-range thereof by weight, based on the weight of the chemical peel component of the skin-enhancing system. One of ordinary skill in the art, however, will appreciate that other ranges are within the scope of the invention.

Thus, each one of the surfactants, alone or in combination, is present in an amount by weight, based on the total weight of the chemical peel component of the skin-enhancing system, from about 2, 3, 4, 5, 6, 7, 8, 9, 10, 11, 12, 13, 14, 15, 16, 17, 18, 19, 20, 21, 22, 23, 24, to about 25 weight percent, including increments and ranges therein and there between.

Thickener

In accordance with the disclosure, the chemical peel component of the skin-enhancing system can include at least one thickener. In some embodiments the chemical peel component comprises two or more thickeners. In some embodiments, the chemical peel component includes one or a combination of thickeners selected from the group consisting of aluminum starch octenylsuccinate, xanthan gum, hydroxyethyl acrylate/sodium acryloyldimethyl taurate copolymer, and combinations thereof. In some particular embodiments, the chemical peel component includes aluminum starch octenylsuccinate, xanthan gum, and hydroxyethyl acrylate/sodium acryloyldimethyl taurate copolymer.

In some embodiments, the chemical peel component of the skin-enhancing system includes one or more thickeners for a water-based system, selected from, for example, acrylates/beheneth-25 methacrylate copolymer, acrylates copolymer, acrylates/C10-30 alkyl acrylate crosspolymer, sodium acrylates copolymer (and) caprylic/capric triglyceride, carbomer, xanthan gum, hydroxypropyl guar, carrageenan, *ceratonia siliqua* (carob) gum, ammonium polyacryloyldimethyl taurate, ammonium acryloyldimethyltaurate/steareth-25 methacrylate crosspolymer, polyacrylate crosspolymer-6 and combinations thereof. In some embodiments the chemical peel component of the skin-enhancing system comprises two or more thickeners.

In some particular embodiments, the one or more thickeners, when present, comprises one or a combination of acrylates/beheneth-25 methacrylate copolymer, and acrylates copolymer.

In accordance with those embodiments that include one or more thickeners, each thickener is present in the composition in an amount from about 0.01% to about 15%, or from about 1% to about 10%, or from about 2% to about 5%, or from about 1% to about 3%, or any suitable combination, sub-combination, range, or sub-range thereof by weight, based on the weight of the chemical peel component. And in some embodiments, the total amount of thickener present in the composition is at least about 3%, or about 4%, or about 10% or more, or in an amount from about 3% to about 15%, from about 3% to about 10%, or from about 3% to about 5%, or any suitable combination, sub-combination, range, or sub-range thereof by weight, based on the weight of the chemical peel component. One of ordinary skill in the art, however, will appreciate that other ranges are within the scope of the invention.

Thus, one or more thickener in the chemical peel component, when present, is present by weight, based on the total weight of the chemical peel component, from about 0.01, 0.02, 0.03, 0.04, 0.05, 0.06, 0.07, 0.08, 0.09, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5, 6, 7, 8, 9, 10, 11, 12, 13, 14, to about 15 percent, including increments and ranges therein and there between.

Other Ingredients

In accordance with the various embodiments, each of the oxidizing and chemical peel components of the skin-enhancing system may further include additional ingredients, generally including, but not limited to, chelating agents, pH adjusters, active components, humectants, antioxidants, plant extracts, plant oils and butters, fragrances, pearlescent agents, odor absorbers, coloring materials, essential oils, vitamins, antimicrobials and preservatives, and combinations of these. Non limiting examples of some of these optional additional ingredients are provided herein below.

Chelating Agent

In some embodiments, one or more other components, such as chelating agents can be present in one or both of the oxidizing component and the chemical peel component of the skin-enhancing system, in amounts from about 0.01% to about 2% by weight, from about 0.02% to about 1.5% by weight, from about 0.02% to about 1%, from about 0.02% to about 0.5%, and from about 0.025 to about 0.15%, or any suitable combination, sub-combination, range, or sub-range thereof by weight, based on the weight of the oxidizing component or the chemical peel component of the skin-enhancing system. In some exemplary embodiments, chelating agents are selected from ethylenediaminetetraacetic acid (EDTA), tetrasodium glutamate diacetate, tetrasodium etidronate, tetrasodium pyrophosphate, pentasodium ethylenediamine tetramethylene phosphonate, sodium staminate and combinations of these.

Thus, one or a combination of chelating agents may be present, by weight, based on the total weight of the skin-enhancing system, each one or the combination present from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 up to about 2 weight percent, including increments and ranges therein and there between.

Optional Actives and Other Ingredients

In some embodiments, there may be one or more additives present in the skin-enhancing system the additive selected from, for example, humectants, such as acetamide MEA, glycols, such as glycerin and propylene glycol; alcohol; anti-microbial components, salicylic acid, alpha acid; antioxidants, including, but not limited to, phenolic compounds, such as chalcones, flavones, flavanones, flavanols, flavonols, dihydroflavonols, isoflavonoids, neoflavonoids, catechins, anthocyanidins, tannins, lignans, aurones, stilbenoids, curcuminoids, alkylphenols, betacyanins, capsacinoids, hydroxybenzoketones, methoxyphenols, naphthoquinones, and phenolic terpenes, resveratrol, curcumin, pinoresinol, ferulic acid, hydroxytyrosol, cinnamic acid, caffeic acid, p-coumaric acid, baicalin (*Scutellaria Baicalensis* root extract), pine bark extract (*Pinus Pinaster* bark/bud extract), ellagic acid; hyaluronic acid and its derivatives; and vitamins and vitamin derivatives, such as tocopherol and ascorbic acid; and combinations thereof.

In some embodiments, additives may include one or a combination of antimicrobial agents and their salts, selected from, for example, chlorphenesin, caprylyl glycol, phenoxyethanol, caprylhydroxamic acid, benzoic acid, salicylic acid, benzyl alcohol, phenethyl alcohol, benzalkonium chloride, 4-hydroxyacetophenone, piroctone olamine, hexyl glycerin, ethylhexylglycerin, octylglycerin, benzylglycerin, 3-heptoyl-2,2-propandiol, and 1,2-hexanediol, and pentylene glycol, and combinations thereof.

In some embodiments, there may be one or more other additives present in the skin-enhancing system, the other components selected from, fillers such as clays; talc; powders, including spherical/silica powders and mineral powders; carbohydrate based gellifying agents; organic thickeners with for instance, anionic, cationic, nonionic, and amphoteric polymeric associative thickeners and combinations thereof; penetrants; sequestrants; fragrances; dispersants; film-forming agents; ceramides; opacifiers and combinations thereof.

In some embodiments, one or more additional ingredients may be selected from the group consisting of chelating agents, pH adjusters, humectants, antioxidants, plant extracts, plant oils and butters, active components, essential oils, vitamins, antimicrobials and preservatives, fragrances, pearlescent agents, odor absorbers, coloring materials, fillers such as clays, talc, powders, including spherical/silica powders and mineral powders, carbohydrate based gellifying agents, organic thickeners, penetrants, sequestrants, fragrances, dispersants, film-forming agents, ceramides, opacifiers, and combinations thereof.

In some particular embodiments, one or more additives in any of the components are selected from the group consisting of sodium hydroxide, trisodium ethylenediamine disuccinate, tocopherol, hydrogen peroxide, chlorophenesin, salicylic acid, phenoxyethanol, bisabolol, sodium hydroxide, trisodium ethylenediamine disuccinate, tocopherol, sodium hyaluronate, propanediol, hydrogen peroxide, and combinations thereof.

In some embodiments, any of the components is essentially free, or free, or devoid of one or more ingredients selected from the group consisting of silicones, including silicone oils, sulfates, and combinations thereof.

Although the aforementioned optional components are given as an example, it will be appreciated that other optional components compatible with cosmetic applications known in the art may be used.

In accordance with the various embodiments, the number of additives present in the skin-enhancing system can range from about 0 to about 50%, from about 0.5 to about 30%, from about 1.5 to about 20%, and from about 5 to about 15%, or any suitable combination, sub-combination, range, or sub-range thereof by weight, based on the weight of the oxidizing component or the chemical peel component of the skin-enhancing system.

In some embodiments, one or more additives, alone or in combination, can be present in one or both of the oxidizing component and the chemical peel component of the skin-enhancing system from about 0.05 to about 50% by weight, from about 0.05% to about 2.5% by weight, from about 0.1 to about 2%, from about 0.25 to about 1.5%, and from about 0.5 to about 1.25%, or any suitable combination, sub-combination, range, or sub-range thereof by weight, based on the weight of the oxidizing component or the chemical peel component of the skin-enhancing system.

In some embodiments, one or more other additives, such as preservatives, vitamins, preservatives, and the like, alone or in combination, can be present in one or both of the oxidizing component and the chemical peel component of the skin-enhancing system from about 0.05 to about 50% by weight, from about 0.05% to about 25% by weight, from about 0.1 to about 10%, from about 0.25% to about 5%, and from about 0.5 to about 3.5%, or any suitable combination, sub-combination, range, or sub-range thereof by weight, based on the weight of the oxidizing component or the chemical peel component of the skin-enhancing system.

Thus, one or a combination of optional additives may be present in one or both of the oxidizing component and the chemical peel component of the skin-enhancing system, by weight, based on the weight of the oxidizing component or the chemical peel component of the skin-enhancing system, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0 0.80, 0.90, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 weight percent, including increments and ranges therein and there between.

Articles of Manufacture

In accordance with the various embodiments, the skin-enhancing system may be provided in a kit or other article of manufacture.

In various embodiments, provided is an article of manufacture for the skin-enhancing system comprising at least first and second separately contained compositions, the first composition comprising an oxidizing component, comprising at least one oxidizing agent and water, and the second composition comprising chemical peel component comprising at least one hydroxy-acid and water, wherein the first and second compositions are contained to be separately dispensed for application to skin, in any order, and wherein the skin-enhancing system may be used according to any one of a number of possible application cycles of the skin-enhancing regimen wherein the oxidizing component is used in conjunction with the chemical peel component, applied in sequence, once or, or more frequently, with applications of at least one of the components on a daily basis for a few or several days.

In some embodiments, each of the oxidizing component and the chemical peel component is provided in a form that is rinse off or leave on and is selected from the group consisting of a suspension, an emulsion cream, a serum, an essence, a gel, and a toner.

In some embodiments, the article of manufacture comprises the first and second compositions each separately contained in a single use container.

In some embodiments, the article of manufacture comprises the first and second compositions each separately contained in a multi-use container.

In some embodiments, the article of manufacture comprises the first and second compositions each separately contained as single units in a plurality of single use containers.

In some embodiments, each of the first and second compositions is contained as one of a mask, liquid, stick, spray, ointment, paste, foam, mousse, shaving cream, wipe, patch, strip, or film-forming product.

In some embodiments, the first composition is an oxidizing component contained for application as a rinse-off mask, and wherein the second composition is a chemical peel component contained for application as a leave-on cream.

In some embodiments disclosed herein, the skincare formulation may be disposed in a first compartment of a sachet and the application surface may be a surface of a second compartment of the sachet, and wherein the first compartment and the second compartment are fluidically separated by a breakable barrier.

In some embodiments disclosed herein, a component of the skin-enhancing system may be coupled to an application surface of an applicator. In some embodiments disclosed herein, the application surface may be a surface of a mask configured to conform to a face of a wearer. In some embodiments disclosed herein, the application surface may be selected from the group consisting of a bristle surface of a brush, a roller surface of a rolling applicator, and a blade surface of a spatula.

It will be appreciated that in the various embodiments of packaging, that the sub compositions that are packaged are maintained as separate until the composition is intended to be applied to keratinous tissue.

In one embodiment, the article of manufacture may be a packet with separate packages or chambers separated by a frangible seal between the chambers. In use, the seal is broken by the user to contact the separately packaged sub compositions and dispense them for application onto the skin. In yet other embodiments, the article of manufacture may be a tube with dual chambers. In yet other embodiments, the article of manufacture may be a dual-chamber pump. In some other embodiments, the packaging for one or both components can be a single container holding a suspension of encapsulated material that is mixed/broken to disperse and mix. And in yet other embodiments, the packaging is otherwise sufficient to retain the each of the components until it is intended to be applied to keratinous tissue.

In some embodiments, the one or both of the first and second parts may be delivered by spray application, or other applicator selected from a pump, or brush.

In accordance with the various embodiments, a component of the skin-enhancing system may be suitable for direct application, or for forming a mask, from form that is a suspension, lotion, cream, serum, essence, gel, stick, spray, ointment, paste, foam, mousse, cream, wipe, patch, strip, film-forming product.

Methods and Regimens for Providing Skin-Smoothing Benefits

The invention also provides, in various embodiments, a regimen for enhancing skin using oxidizer and acid application components, comprising applying to a region of skin excluding areas of skin around an eye (a) a first composition comprising an oxidizing component that includes an oxidizing agent and water; and (b) a second composition comprising a chemical peel component that includes one or a combination of hydroxy-acids and water, wherein the first and second compositions are applied sequentially, in any order. In some embodiments, the oxidizing component is applied first, followed by the chemical peel component, and in other embodiments, the chemical peel component is applied first, followed by the oxidizing component.

In some embodiments, the steps of the regimen further include (c) rinsing the skin after application of at least one of the first and second compositions, and include (a), (b) and (c) in any order, and wherein the step (c) may be repeated.

The regimen may be selected from one or a combination of application cycles.

In some embodiments, after a first instance of step (a), step (b) is repeated once daily, over a plurality of days.

In some embodiments, step (a) is repeated once every third, fourth or fifth day and wherein step (b) is skipped on the days that step (a) is repeated.

In one embodiment of a regimen cycle, after a first instance of step (a), step (b) is repeated once daily, over a plurality of days. For example, in a particular embodiment, on day 1, the oxidizing component is applied first, followed by the chemical peel component, and thereafter, on at least one or more subsequent days, the chemical peel component is applied each day.

In one embodiment of a regimen cycle, step (a) is repeated once every third, fourth or fifth day and step (b) is skipped on the days that step (a) is repeated. For example, in a first embodiment of a regimen cycle, on day 1, the oxidizing component is applied first, followed by the chemical peel component, and thereafter, on days 2, 3 and 4, the chemical peel component is applied each day, and on day 5 the oxidizing component is applied followed by the chemical peel component, and then on days 6 and 7 the chemical peel cream is applied. And, for example, in a second embodiment of a regimen cycle, on day 1, the oxidizing component is applied first, followed optionally by the chemical peel component, and thereafter, on days 2-7, the chemical peel component is applied each day. And for example, in a third embodiment of a regimen cycle, on day 1, the oxidizing component is applied first, and thereafter, on days 2, 3 and 4, the chemical peel component is applied each day, and on day 5 the oxidizing component is applied, and then on days 6 and 7 the chemical peel cream is applied.

Other regimen cycles are possible and the foregoing examples are not limiting.

In some embodiments, the regimen is practiced for at least one day.

In some embodiments, the regimen is practiced for at least three days, with at least one application of at least one component on each day. In some embodiments, the regimen is practiced for at least three or more days, with at least one application of at least one component over the time period, wherein one or more days may not include application of any component.

In some embodiments, the regimen is practiced for at least 28 days, with at least one application of at least one component on each day. In some embodiments, the regimen is practiced for at least 28 days, with at least one application of at least one component over the time period, wherein one or more days may not include application of any component.

In some embodiments, a component of the skin-enhancing system is applied to the keratinous tissue, for example skin of the body or face, in some particular embodiments on the face and generally excluding the eye area, at a temperature of about 15° C. to about 30° C., or from about 20° C. to about 25° C.

The skin-enhancing system is suitable for home-use or home application. As such, a component of the skin-enhancing system according to the present invention is applied by a non-professional or is self-applied in a non-clinical environment.

A component of the skin-enhancing system may be applied in any manner, for example, by pasting, spraying, wiping, dispensing, etc. (hereinafter "applying") on the keratinous tissue. This can typically be accomplished with, for example, a spray bottle, an absorbent cotton swab wetted with the concentrated solution, with a solution-wetted sable brush or by gentle wiping with a solution-wetted absorbent fibrous material, such as a gauze square or nonwoven pad, but other solution application techniques that coat the skin with the solution, in a uniform manner, are also feasible.

A component of the skin-enhancing system that is intended for leave-on application is applied and allowed to air dry without removal until the user employs their usual cleansing routine. Of course, a component of the skin-enhancing system may optionally be removed after application and some selected interval of time, though the results may not be as desirable. Drying may be promoted by directing a gentle stream of air, warm air, onto the treated area or by other analogous procedures. A single uniform application of a component of the skin-enhancing system to the keratinous tissue is generally sufficient. Additional or multiple applications either before or immediately after the applied solution has dried are normally unnecessary but may be useful in some situations, e.g., in applications to keratinous tissue on other parts of the body other than the face or in applications to keratinous tissue severely in need of peeling. For rinse-off forms of a component of the skin-enhancing system, the component should be rinse off, in particular prior to applying any other composition or product to the skin.

EXAMPLES

Example 1: Raw Materials

Percentages of each ingredient as may be exemplified in the following examples are shown as amount of active, wherein the raw materials may be present in an amount that is equal to the amount of active, or if the raw material has a concentration of active that is less than 100% then the composition includes the raw material that includes active and a suitable solvent, wherein the concentration of active in the raw material is provided herein below.

The following raw materials for ingredients as shown in the TABLES herein include actives present at less than 100%, as follows:

TABLE 1

| Representative Raw Materials Percent Active | |
| --- | --- |
| Raw Material | Percent Active (%) |
| Hydrogen Peroxide | 50 |
| Pentasodium Ethylenediamine Tetramethylene Phosphonate | 33 |
| Tetrasodium Glutamate Diacetate | 47.5 |
| Phosphoric Acid | 85 |
| Stearic Acid | 53 |
| Trisodium Ethylenediamine Disuccinate | 37 |
| Hydroxyethyl Acrylate/Sodium Acryloyldimethyl Taurate Copolymer | 90 |
| Lactic Acid | 90 |
| Dicaprylyl Ether | 99.97 |
| Glycolic Acid | 70 |

Example 2: Inventive Compositions

Oxidizing Component

TABLE 2

| | Oxidizing component Cream Embodiments (in the form of creamy emulsion rinse-off cleanser) | | | |
| --- | --- | --- | --- | --- |
| INGREDIENT | OX CREAM BASE | OX CREAM A 50% Oil | OX CREAM B 20% Oil | OX CREAM C 50% Oil |
| STEARETH-2 | 3.5 | 3.50 | 3.50 | 1.75 |
| STEARETH-20 | 1.5 | 1.50 | 1.50 | 0.75 |
| HYDROGEN PEROXIDE | 4.0 | 4.00 | 4.00 | 4.00 |
| C15-19 ALKANE | 50.00 | 50.00 | 20.00 | 50.00 |
| SCLEROTIUM GUM | 1.0 | 1.00 | 1.00 | 1.00 |
| PENTASODIUM ETHYLENEDIAMINE TETRAMETHYLENE PHOSPHONATE | 0.3 | | | |
| TETRASODIUM GLUTAMATE DIACETATE | | 0.15 | 0.15 | 0.15 |
| OTHER INGREDIENTS (PHOSPHORIC ACID, SODIUM PHOSPHATE, TETRASODIUM PYROPHOSPHATE, TOCOPHEROL, SODIUM | 0.7 | 0.6 | 0.6 | 0.6 |

TABLE 2-continued

Oxidizing component Cream Embodiments (in the
form of creamy emulsion rinse-off cleanser)

| INGREDIENT | OX CREAM BASE | OX CREAM A 50% Oil | OX CREAM B 20% Oil | OX CREAM C 50% Oil |
|---|---|---|---|---|
| SALICYLATE) | | | | |
| WATER | qs | qs | qs | qs |

TABLE 3

Oxidizing component Toner Embodiments
(in the form of leave-on toner)

| INGREDIENT | OX TONER (wt %) |
|---|---|
| Hydrogen Peroxide | 4 |
| Water | 96 |

Chemical Peel Component: Emulsion Cream and Liquid
Forms

TABLE 4

Peel Component Cream Embodiments (in the form of creamy emulsion leave-on moisturizer)

| INGREDIENT | PEEL MOISTURIZER BASE | PEEL MOISTURIZER 1 10% Glycerin | PEEL MOISTURIZER 2 5% Glycerin | PEEL MOISTURIZER 3 7% Glycerin |
|---|---|---|---|---|
| GLYCERIN | 10.00 | 10.00 | 5.00 | 7.00 |
| GLYCOLIC ACID | 14.28 | 14.28 | 14.28 | 14.28 |
| SALICYLIC ACID | 0.45 | 0.45 | 0.45 | 0.45 |
| C12-15 ALKYL BENZOATE | 4.00 | 4.00 | 4.00 | 4.00 |
| CAPRYLIC/CAPRIC TRIGLYCERIDE | 5.00 | 5.00 | 5.00 | 5.00 |
| THEOBROMA CACAO (COCOA) SEED BUTTER | 1.00 | 1.00 | 1.00 | 1.00 |
| BUTYROSPERMUM PARKII (SHEA) BUTTER | 2.00 | 2.00 | 2.00 | 2.00 |
| COCO-CAPRYLATE/CAPRATE | 3.00 | 3.00 | 3.00 | 3.00 |
| GLYCERYL STEARATE | 2.00 | 2.00 | 2.00 | 2.00 |
| CETEARYL ALCOHOL (and) CETEARETH-20 | 1.00 | 1.00 | 1.00 | 1.00 |
| GLYCERYL STEARATE (and) PEG-100 STEARATE | 2.00 | 2.00 | 2.00 | 2.00 |
| STEARIC ACID | 1.00 | 1.00 | 1.00 | 1.00 |
| POLYSORBATE 20 | 2.00 | 2.00 | 2.00 | 2.00 |
| SODIUM HYDROXIDE | 4.5 | 2.25 | 2.25 | 2.25 |
| XANTHAN GUM | 0.20 | 0.20 | 0.20 | 0.20 |
| HYDROXYETHYL ACRYLATE/SODIUM ACRYLOYLDIMETHYL TAURATE COPOLYMER | 4.00 | 4.00 | 4.00 | 4.00 |
| WATER | qs | qs | qs | qs |
| OTHER INGREDIENTS (PHENOXYETHANOL, TRISODIUM ETHYLENEDIAMINE DISUCCINATE, TOCOPHEROL, CHLORPHENESIN) | 1.40 | 1.40 | 1.40 | 1.40 |

TABLE 5

Peel Component Toner Embodiments (in the form leave-on toner)

| INGREDIENT | PEEL TONER 1 (MODIFIED JESSNER-TYPE HOME PEEL) | PEEL TONER 2 |
|---|---|---|
| POTASSIUM HYDROXIDE | 2.00 | |
| LACTIC ACID | 11.11 | |

TABLE 5-continued

Peel Component Toner Embodiments (in the form leave-on toner)

| INGREDIENT | PEEL TONER 1 (MODIFIED JESSNER-TYPE HOME PEEL) | PEEL TONER 2 |
|---|---|---|
| SALICYLIC ACID | 0.45 | |
| PHENYLETHYL RESORCINOL | 0.75 | |
| ALCOHOL DENAT. | 10.69 | |

TABLE 5-continued

Peel Component Toner Embodiments (in the form leave-on toner)

| INGREDIENT | PEEL TONER 1 (MODIFIED JESSNER-TYPE HOME PEEL) | PEEL TONER 2 |
|---|---|---|
| WATER | 75.00 | |
| LACTIC ACID | | 4.20 |

TABLE 5-continued

Peel Component Toner Embodiments (in the form leave-on toner)

| INGREDIENT | PEEL TONER 1 (MODIFIED JESSNER-TYPE HOME PEEL) | PEEL TONER 2 |
|---|---|---|
| SALICYLIC ACID | | 0.20 |
| BETAINE | | 0.93 |
| SODIUM CHLORIDE | | 0.93 |
| DICAPRYLYL ETHER | | 1.86 |
| MACADAMIA TERNIFOLIA SEED OIL | | 0.47 |
| SQUALANE | | 4.64 |
| GLYCERIN | | 4.65 |
| PROPANEDIOL | | 2.79 |
| PENTYLENE GLYCOL | | 3.72 |
| CARRAGEENAN | | 0.093 |
| SODIUM HYALURONATE | | 0.0093 |
| SODIUM HYDROXIDE | | 1.32 |
| FRAGRANCE | | 0.029 |
| WATER | | 74.15 |

The inventive the skin-enhancing system is employed using any combination of an oxidizing component and a chemical peel component, such as but not limited to selection from the examples provided in the tables herein above. Below, TABLE 6 provides a list of inventives that are combinations of oxidizing component and chemical peel component formulations from the above tables, as well as comparative compositions that include oxidizing or chemical peel components alone, wherein the examples in TABLE 6 are selected from for use in the test studies shown in the Examples below. As used herein, the term "Peel Moisturizer" refers to moisturizing forms of the chemical peel component, for example, but not limited to creamy emulsion forms thereof.

TABLE 6

Inventive and Comparative Test Compositions (Inventive System Compositions include the specified Oxidizing and Chemical Peel components which are employed individually for comparisons in the examples as the specified Comparative compositions)

| TEST EXAMPLE | INGREDIENTS | USED IN EXAMPLE BELOW | Part A OXIDIZING COMPONENT | Part B CHEMICAL PEEL COMPONENT |
|---|---|---|---|---|
| Acid Control | 70% Glycolic Acid | Examples 3 & 4 | NA | NA |
| Comp 1 | Peroxide; 50% oil | Examples 3, 4 & 6 | OX CREAM BASE | |
| Comp 2 | Acids; high oil | Examples 3, 4 & 6 | NA | PEEL MOISTURIZER BASE |
| Comp 3 (Jessner type) | Acids; nominal oil | Example 3 | NA | PEELTONER 1 (Jessner type) |
| Comp 4 | Acids; high oil | Example 4 | NA | PEEL MOISTURIZER 1 |
| Comp 5 | Peroxide; nominal oil | Example 4 | OX TONER | |
| INVENTIVE 1 | | Examples 3, 4 & 6 | OX CREAM BASE | PEEL MOISTURIZER BASE |
| INVENTIVE 2 | | Example 3 | OX CREAM BASE | PEEL TONER 1 (Jessner type) |
| INVENTIVE 3 | | Example 4 | OX TONER | PEEL MOISTURIZER 1 |

Example 3: In Vitro Stratum Corneum Testing for Lipid Disorganization w/Cream and Toner Forms of Chemical Peel Component In Vitro Stratum Corneum (SC) testing to evaluate lipid disorganization was conducted, and $\Delta T$ was determined using differential scanning calorimetry (DSC), measuring the heat change associated with thermal denaturation when heated at a constant rate. Compositions and control samples were applied on in vitro SC surface (~0.1 g/sample) for 15 min at 75% relative humidity. According to applications that included use of oxidizing component followed by chemical peel components, the applications were made in series (i.e., not simultaneous/in parallel). Following single or sequential applications, the SC surface was wiped clean and rinsed with distilled water and allowed to dry overnight at 75% relative humidity. The DSC profile was measured from 20° C. to 120° C. at 5° C./min to provide $\Delta T$ for lipid related peaks at 70-75° C. and 80-85° C. $\Delta T$ is calculated by the change in peak temperature by comparing the temperature of untreated control versus the compositions as listed in TABLE 7, below. Results are shown in TABLE 7 and in FIG. 1.

TABLE 7

Lipid Disorganization: Oxidizing Component (Emulsion Cream Form) with Chemical Peel Component leave-on creamy emulsion moisturizer and toner forms.

| Composition | Ingredients | $\Delta T$ |
|---|---|---|
| Acid Control | 70% Glycolic Acid | −9.968 +/− 0.47 |
| Comp 1 | Peroxide; 50% oil | −3.823 +/− 1.33 |
| Comp 2 | Acids; high oil | −5.99367 +/− 1.11 |

TABLE 7-continued

| Composition | Ingredients | ΔT |
|---|---|---|
| | Lipid Disorganization: Oxidizing Component (Emulsion Cream Form) with Chemical Peel Component leave-on creamy emulsion moisturizer and toner forms. | |
| INVENTIVE 1 | Comp 1 (OX CREAM BASE) followed by Comp 2 (PEEL MOISTURIZER BASE) | −13.8335 +/− 1.54 |
| Comp 3 | Acids; nominal oil | −6.6205 +/− 0.57 |
| INVENTIVE 2 | Comp 1 (OX CREAM BASE) followed by Comp 3 (PEEL TONER 1) | −14.345 +/− 1.51 |

Referring to TABLE 7, the study demonstrates the synergistic effect on skin rejuvenation in an SC model when a rinse-off form of the oxidizing component is used with a leave-on emulsion moisturizer or toner chemical peel component.

Figure 2:
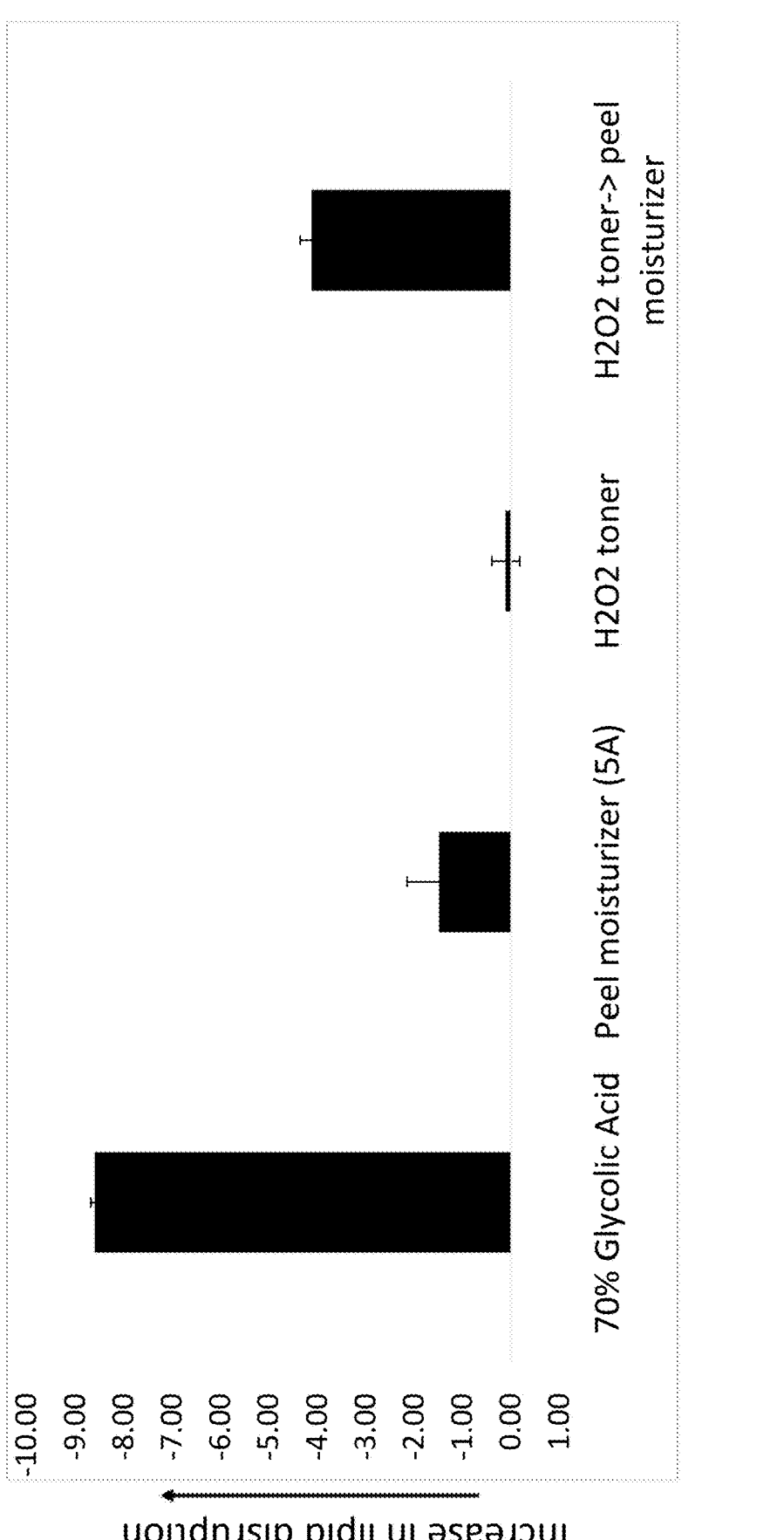
FIG. 2 is a bar graph showing results according to the first study.

Example 4: In Vitro Stratum Corneum Testing for Lipid Disorganization w/Cream and Toner Forms of Oxidizing Component In Vitro Stratum Corneum testing to evaluate lipid disorganization was conducted as described above. Studies were conducted with each of the test compositions as listed in TABLE 8, to evaluate effect of the compositions on the stratum corneum. Results are shown in TABLE 8 and FIG. 2.

TABLE 8

| Composition | Ingredients | ΔT |
|---|---|---|
| | Lipid Disorganization: Oxidizing Component Toner Form with Chemical Peel Component Emulsion (Moisturizer) Form | |
| Acid Control | 70% Glycolic Acid | −8.60 +/− 0.08 |
| Comp 4 | Acids; high oil | −1.49 +/− 0.66 |
| Comp 5 | Peroxide; nominal oil | −0.11 +/− 0.29 |
| INVENTIVE 3 | Comp 5 (OX TONER) followed by Comp 4 (PEEL MOISTURIZER 1) | −4.13 +/− 0.24 |

Referring to TABLE 8, the study demonstrates the synergistic effect on skin rejuvenation in an SC model when a toner form of the oxidizing component is used with a leave-on emulsion moisturizer chemical peel component.

The results shown in this Example 4, taken together with the results of Example 3, demonstrate that a consistently higher level of lipid disorganization is observed in SC that is treated with the regimen that includes use of a skin-enhancing system that includes a single application of a hydrogen peroxide containing oxidizing component followed by a single application of a chemical peel component, regardless of the formulation forms. More particularly, the data clearly show that there is a synergistic (i.e., greater than additive) effect on skin rejuvenation as evidenced by lipid disorganization, when various combinations of leave-on and rinse-off forms of the oxidizing component and chemical peel components are used.

Example 5: Ex Vivo Skin Study

Compositions that include Acid Control, Comp 1, Comp 3 and INVENTIVE 2 were evaluated in an ex vivo study to show biological effects on skin samples.

Fresh post-abdominoplasty normal human skin samples were acquired, defatted, and cleaned. Explants were made using a 12 mm biopsy punch. Three punches were produced for each application condition with two different timepoints: Day 1 and Day 7. Prior to placing the skin tissue into culture, biopsies were treated with different applications according to the following procedure:

Comp 1 (OX CREAM BASE): 50 μL of Part A and 50 μL of Part B was applied for 15 minutes. After application, the formula was removed and the sample surfaces were cleaned and dried before returning to culture.

Comp 3 (PEEL TONER 1): A sterile cotton tip applicator was soaked in Modified Jessner Home Peel and formula was topically applied to the ex vivo skin samples for 10 minutes. After application, the explant surfaces were cleaned and dried before returning to culture.

INVENTIVE 2 (OX CREAM BASE followed by PEEL TONER 1): 50 μL of Part A and 50 μL of Part B was applied for 15 minutes. After application, the formula was removed and the sample surfaces were cleaned and dried before returning to culture.

All ex vivo skin explants were cultured at air-liquid interface in Dulbecco's Modified Eagle's Medium (DMEM with 10% Fetal Bovine Serum and 1% Penicillin-Streptomycin) at 37° C. On day 1 and day 7, samples were bisected and placed in formalin and OCT gel for hematoxylin and eosin stain (H&E) immunofluorescent staining and frozen sectioning, respectively. Immunofluorescent staining against involucrin was conducted by first fixing frozen section samples for 10 minutes at −20° C. in methanol. Slides were then permeabilized with 0.1% Triton-X in PBS. The samples were blocked with 10% normal goat serum for one hour at room temperature. Tissue sections were then incubated with Rabbit Polyclonal to Involucrin (Abcam, ab81468, 1:150) for one hour. The slides were then incubated with the secondary antibody using the Goat Anti-Rabbit IgG H&L Alexa Fluor 594 in a 1/200 dilution in blocking solution and counterstained with DAPI. All sections were then imaged using a fluorescent microscope (Leica DM500, Wetzlar, Germany).

All samples were examined without and with involucrin, which is a key biomarker indicating the kinetics of skin turnover.

Figure 3:
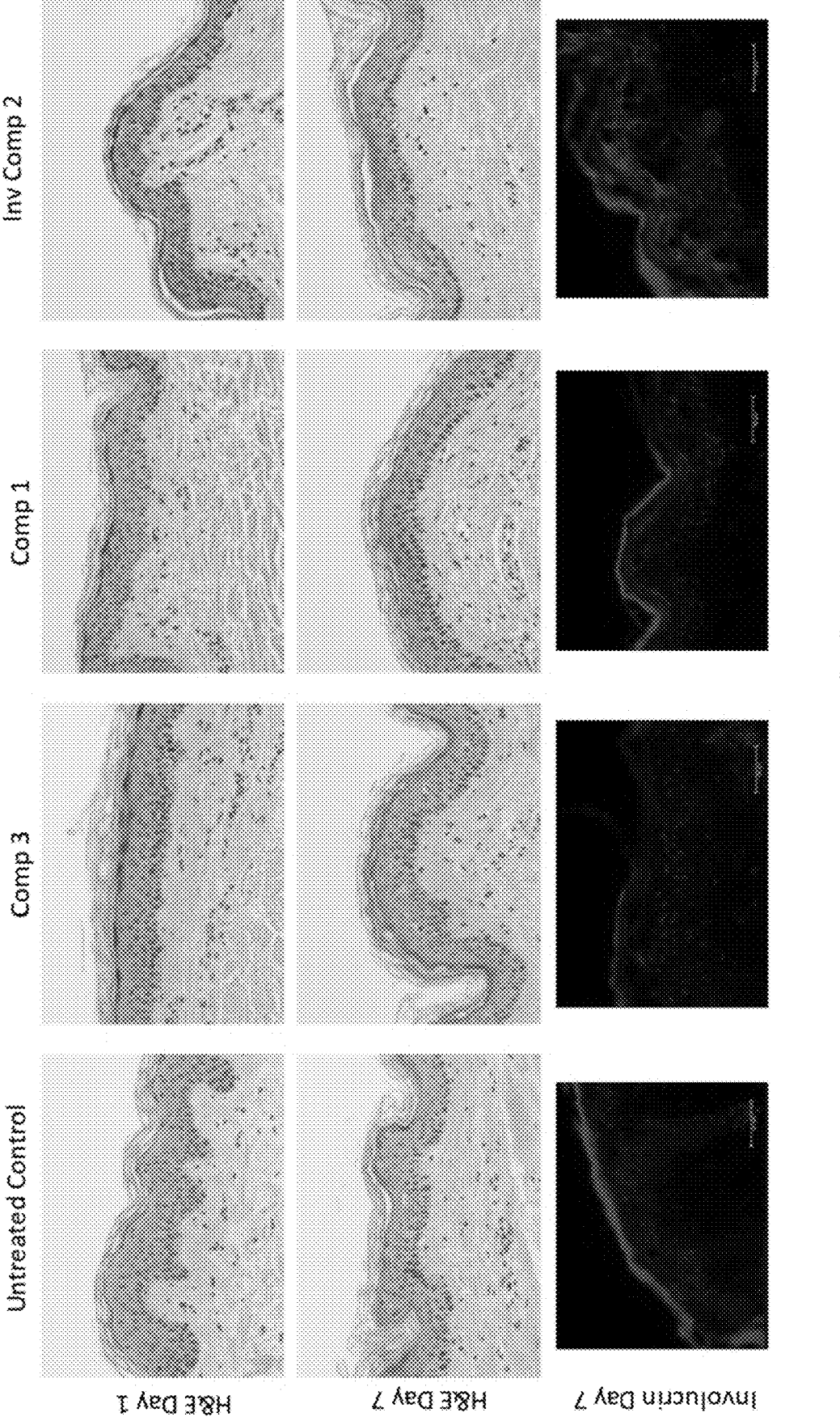
FIG. 3 includes color photographic images of treated skin tissue demonstrating effect of the inventive skin-enhancing regimen.

Referring now to the drawings, FIG. 3 shows microscopy images of the tested samples at Day 1 (Baseline) for H&E (A=Acid control, B=Comp 3, C=Comp 1, and D=INVENTIVE 2) and at Day 7 for H&E and staining against Involucrin (E=Acid control, F=Comp 3, G=Comp 1, and H=INVENTIVE 2. The H&E staining results suggests that each of the applications including Comp 3 alone, Comp 1 alone, and INVENTIVE 2 do not induce any obvious signs of cellular/tissue damage. Further analysis of involucrin expression at D7, as also shown in FIG. 3, suggests that the formulation of INVENTIVE 2 according to the disclosure exhibited an enhanced effect as compared to Comp 1 and Comp 3 used alone, wherein, without being bound by theory, it is contemplated that the inventive application results in elevation of the involucrin level greater than the level observed for each of the comparatives alone. This suggests that the inventive application with the formulation of INVENTIVE 2 according to the disclosure has the potential to synergistically boost the renewal of skin barrier when viewed together with the SC data from the prior Examples.

Example 6: Clinical Study

In the study, an application regimen included a twice per week application of an oxidizing component in rinse off mask form, and a daily application of a chemical peel component in leave on moisturizer form was followed and compared with a regimen that included daily application of a peel moisturizer chemical peel component alone (without any oxidizing component). The composition employed were Comp 4 (PEEL MOISTURIZER 1) and INVENTIVE 3 (Comp 5 (OX TONER) followed by Comp 4 (PEEL MOISTURIZER 1)).

Figure 4:
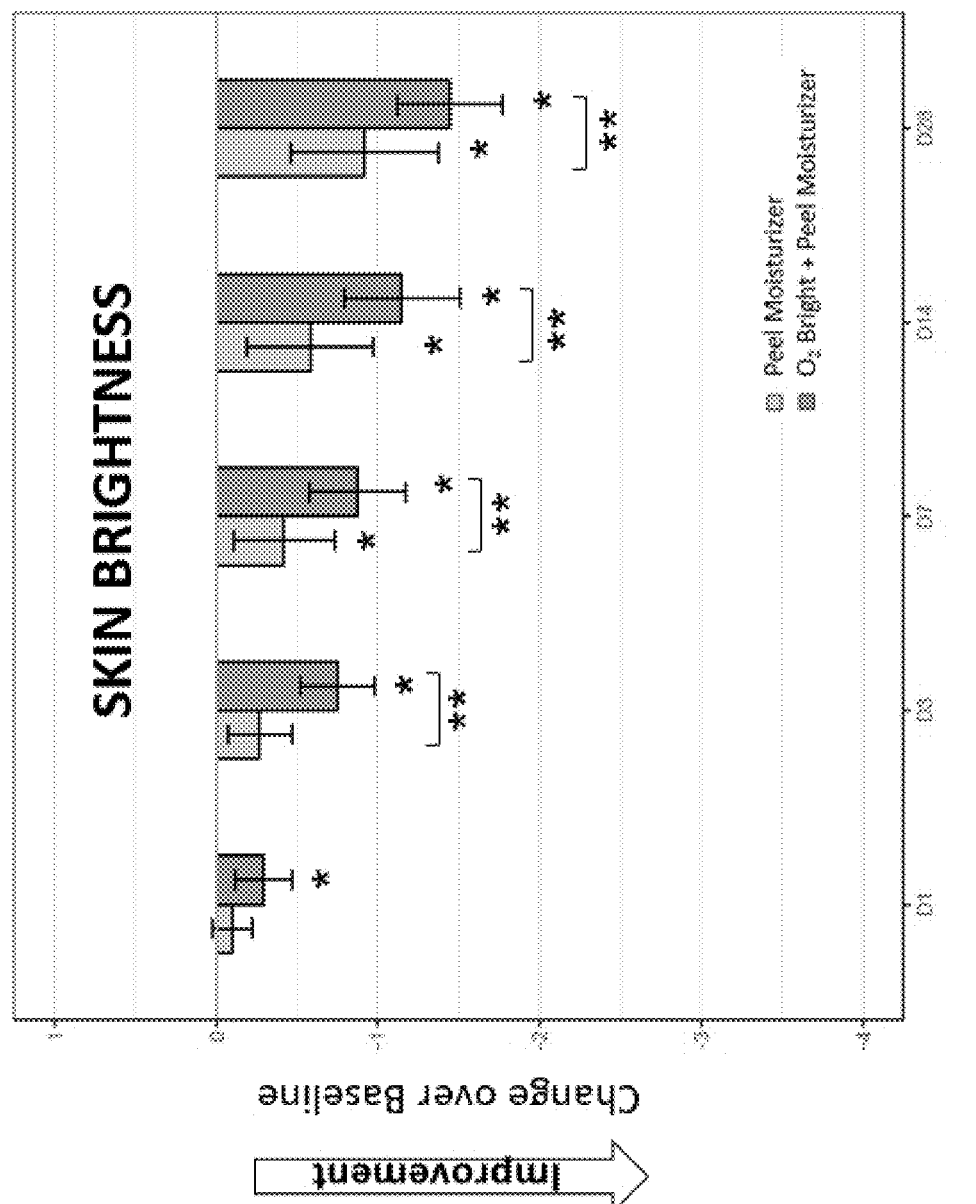
FIG. 4 shows the clinical grading results of skin brightness at different time points according to the clinical study.
Figure 5:
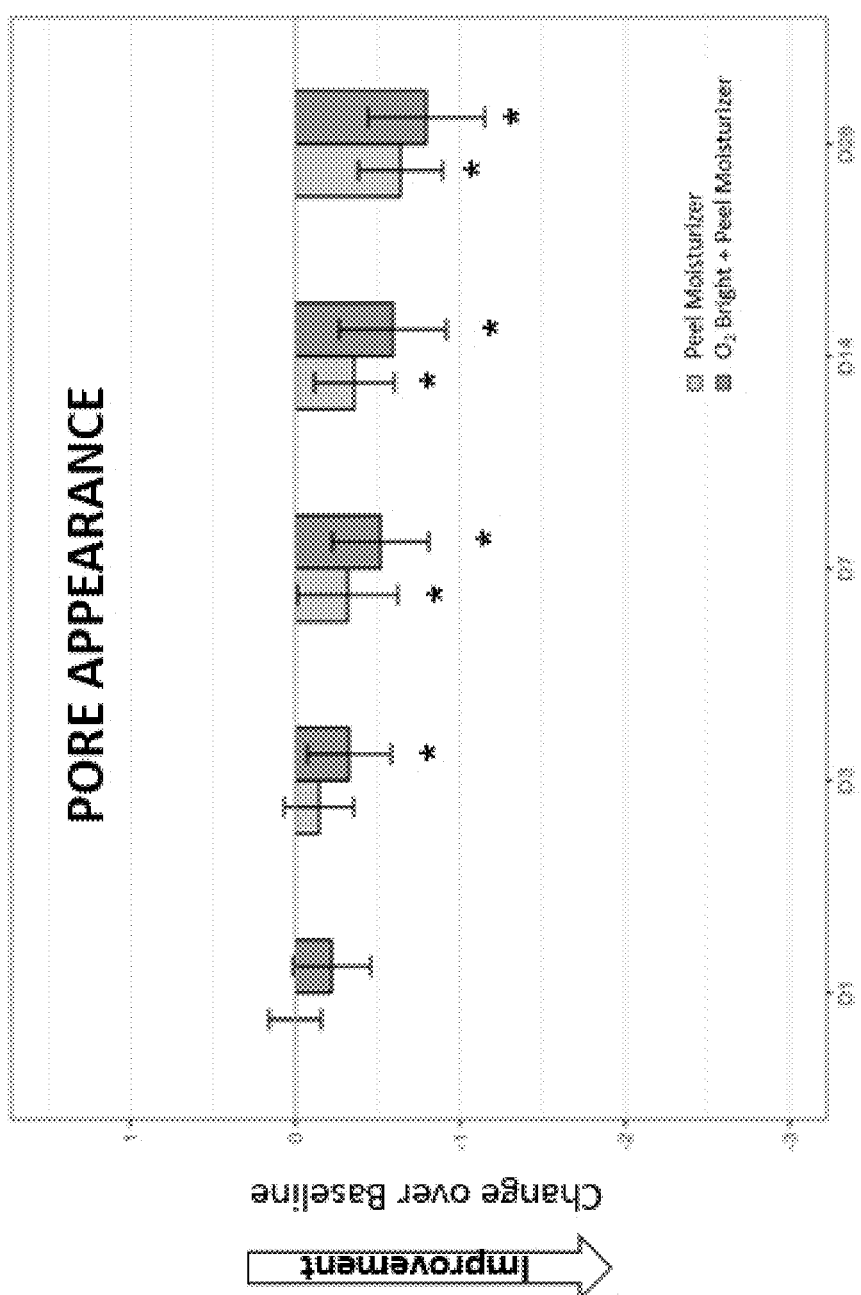
FIG. 5 shows the clinical grading results of pore appearance at different time points according to the clinical study.
Figure 6:
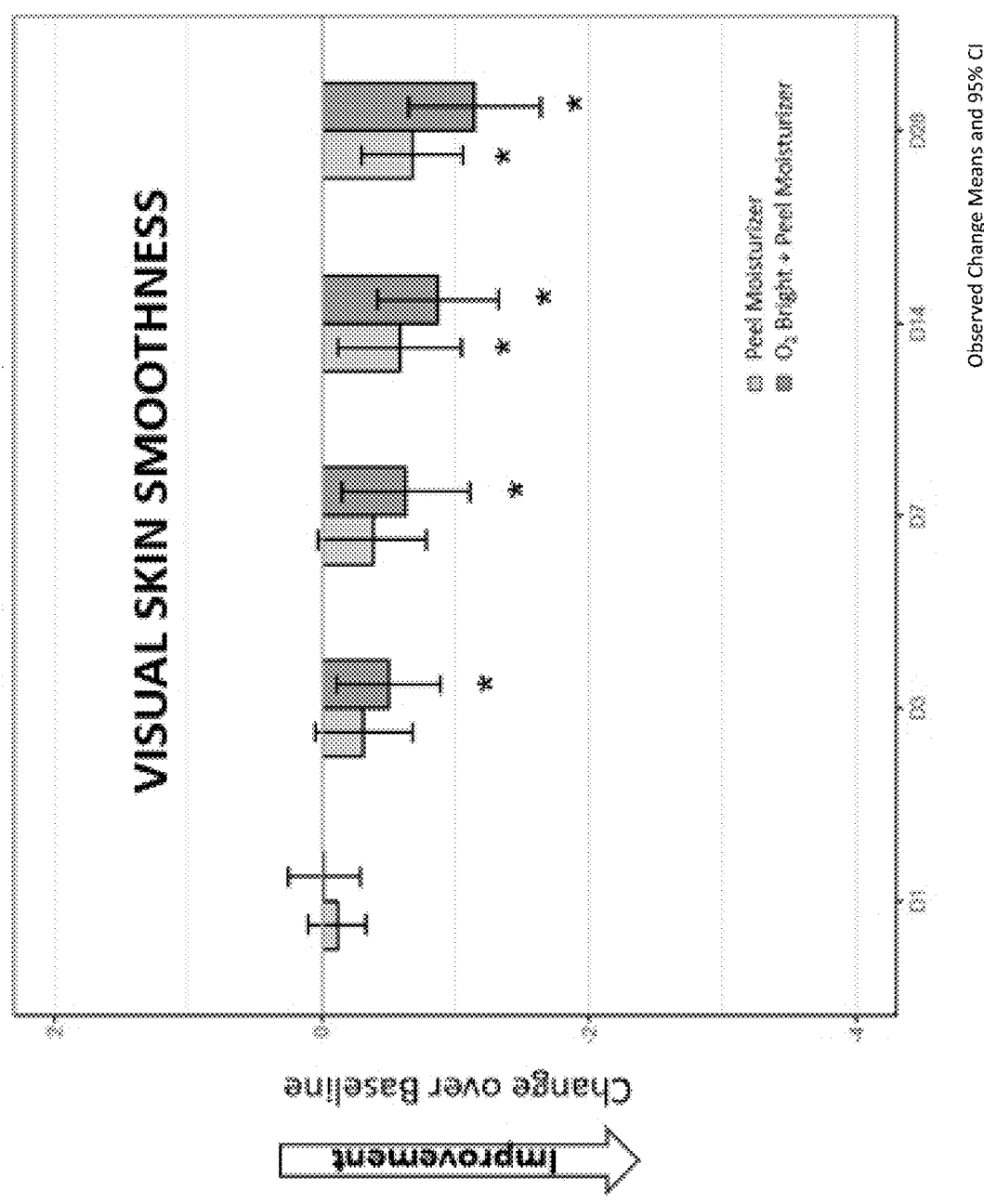
FIG. 6 shows the clinical grading results of visual skin smoothness at different time points according to the clinical study.
Figure 7:
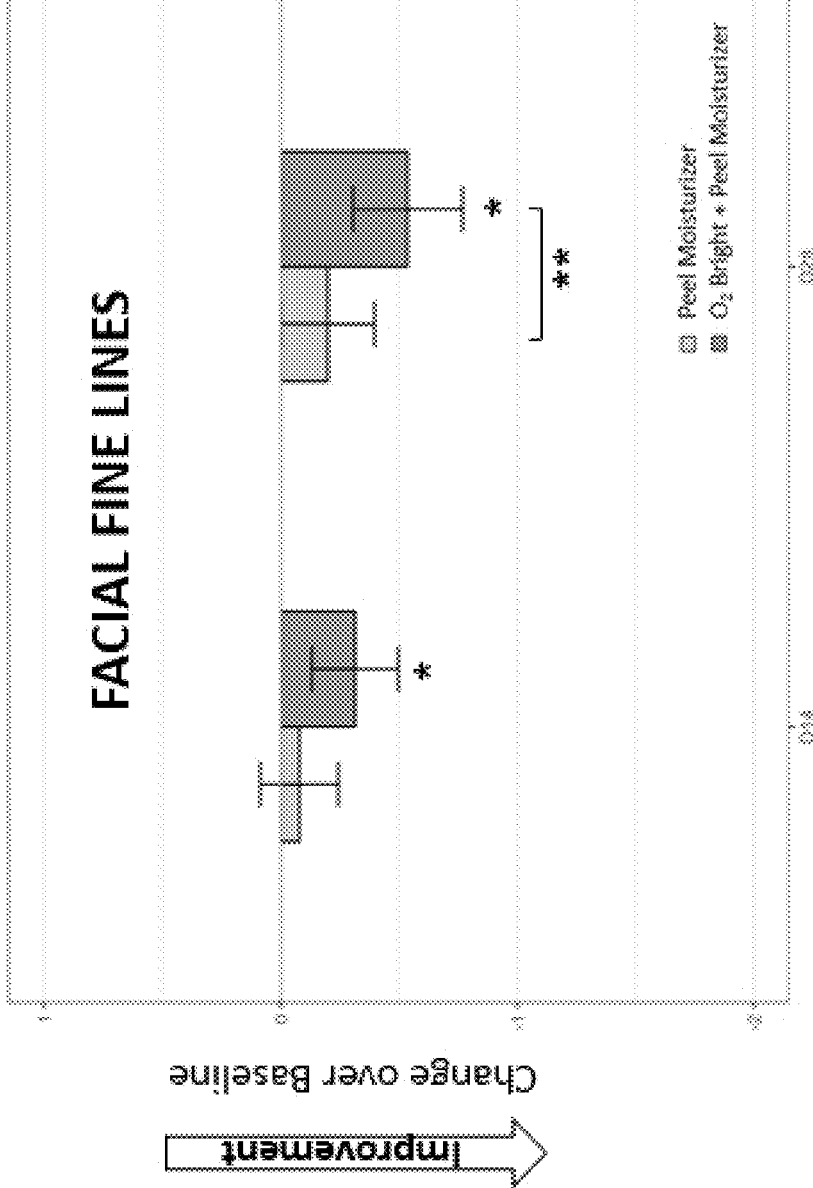
FIG. 7 shows the clinical grading results of facial fine lines at different time points according to the clinical study.
Figure 8:
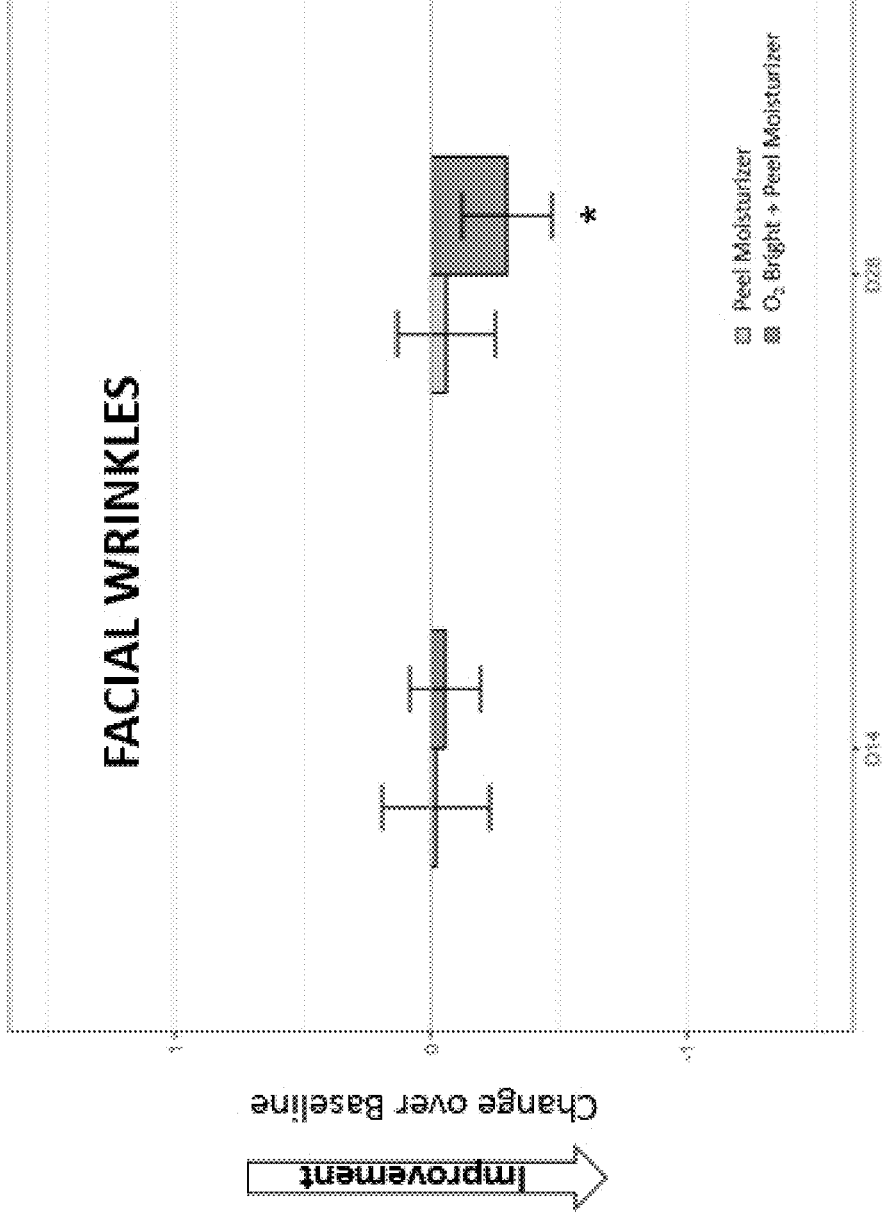
FIG. 8 shows the clinical grading results of facial wrinkles at different time points according to the clinical study.

FIG. 4 shows the effects of the inventive system on skin brightness reflecting, FIG. 5 shows the effects of the inventive system on pore appearance, FIG. 6 shows the effects of the inventive system on visual smoothness, FIG. 7 shows the effects of the inventive system on fine lines, and FIG. 8 shows the effects of the inventive system on wrinkles. The results of following the exemplified inventive regimen over the timeframe from a few days up to 28 days demonstrated rapid and statistically significant improvement in skin brightness within one day, improvement in pore appearance and visual smoothness within three days, improvement in facial fine lines within fourteen days, and improvement in facial wrinkles within twenty-eight days. The results show that the inventive system and regimen provided statistically significant enhancement in skin brightness and global facial fine lines as compared to use of the moisturizing peel alone. These results as shown in Example 5 are consistent with the in vitro results described in Examples 3-5.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising," "consisting essentially of" and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g., "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention is not limited to the particular embodiment disclosed as the best mode contemplated for carrying out this invention, but that the invention will include all embodiments falling within the scope of the appended claims.

What is claimed is:

1. An article of manufacture for a skin-enhancing system comprising:
    at least first and second separately contained compositions:
        the first composition comprising an oxidizing component, comprising:
            at least one oxidizing agent selected from the group consisting of hydrogen peroxide, urea peroxide, carbamide peroxide, PVP hydrogen peroxide, and combinations thereof, at least one non-silicone oil present in the oxidizing component in a range from about 20% to about 80%, by weight, based on the total weight of the oxidizing component; and
water; and
the second composition comprising:
a chemical peel component comprising at least one hydroxy acid; and water,
wherein the first composition is a creamy emulsion;
wherein the first and second compositions are contained to be separately dispensed for application to skin, in any order,
wherein the first composition is free of salicylic acid and free of anionic polymeric associative thickeners other than hyaluronic acid, carrageenan, or combinations thereof, and may optionally include xanthan gum, carbomer or combinations thereof,
wherein the first composition is free of oxidizing agents other than the hydrogen peroxide, the urea peroxide, the carbamide peroxide, the PVP hydrogen peroxide, or combinations thereof,
wherein the second composition is free of hydrogen peroxide and free of anionic polymeric associative thickeners other than hyaluronic acid, carrageenan, or combinations thereof, and may optionally include xanthan gum, carbomer, or combinations thereof, and
wherein the skin-enhancing system may be used according to any one of a number of possible application regimens wherein the oxidizing component is used in conjunction with the chemical peel component, applied in sequence, once or, or more frequently, with applications of at least one of the components on a daily basis for a few or several days.

2. The article of manufacture according to claim 1, wherein the at least one oxidizing agent in the oxidizing component includes the hydrogen peroxide.

3. The article of manufacture according to claim 1, wherein the at least one oxidizing agent in the oxidizing component is present from about 1% to about 10% by weight, based upon the total weight of the oxidizing component.

4. The article of manufacture according to claim 1, wherein the at least one hydroxy acid in the chemical peel component is selected from the group consisting of alpha-hydroxy acids, beta-hydroxy acids, and combinations thereof.

5. The article of manufacture according to claim 1, wherein the at least one hydroxy acid in the chemical peel component comprises at least one alpha-hydroxy acid present from about 4% to about 15% by weight, based upon the total weight of the chemical peel component.

6. The article of manufacture according to claim 5, wherein the at least one hydroxy acid in the chemical peel component further comprises at least one beta-hydroxy acid present from about 0.1% to about 2% by weight, based upon the total weight of the chemical peel component.

7. The article of manufacture according to claim 1, wherein the at least one oxidizing agent in the oxidizing component is present from about 1% to about 10% by weight, based upon the total weight of the oxidizing component, the at least one non-silicone oil includes C15-19 alkane, and the oxidizing component further comprises at least one chelating agent, and at least one additional ingredient selected from the group consisting of water based solvents, surfactants, thickeners, pH adjusters, humectants, antioxidants, plant extracts, plant oils, plant butters, fragrances, pearlescent agents, odor absorbers, coloring materials, essential oils, vitamins, antimicrobials, preservatives, and combinations thereof.

8. The article of manufacture according to claim 1, wherein the at least one hydroxy acid in the chemical peel component further comprises at least one additional hydroxy acid selected from the group consisting of at least one alpha-hydroxy acid, at least one beta-hydroxy, and at least one poly-hydroxy acid.

9. The article of manufacture according to claim 1, wherein the at least one hydroxy acid in the chemical peel component further comprises at least one additional hydroxy acid selected from the group consisting of at least one alpha-hydroxy acid present from about 4% to about 15%, at least one beta-hydroxy acid present from about 0.1% to about 2%, and at least one poly-hydroxy acid present from about 4% to about 15%, all amounts by weight, based upon the total weight of the chemical peel component, and combinations thereof, wherein the chemical peel component further comprises at least one additional ingredient selected from the group consisting of oils, water based solvents, surfactants, thickeners, phenylethyl resorcinol, chelating agents, pH adjusters, humectants, antioxidants, plant extracts, plant oils, plant butters, fragrances, pearlescent agents, odor absorbers, coloring materials, essential oils, vitamins, antimicrobials, preservatives, and combinations thereof.

10. The article of manufacture according to claim 1, wherein each of the oxidizing component and the chemical peel component is provided in a form that is rinse off or leave on and the chemical peel is selected from the group consisting of a suspension, an emulsion cream, a serum, an essence, a gel, and a toner.

11. The article of manufacture according to claim 1, wherein the article of manufacture comprises the first and second compositions each separately contained in a single use container.

12. The article of manufacture according to claim 1, wherein the article of manufacture comprises the first and second compositions each separately contained in a multi-use container.

13. The article of manufacture according to claim 1, wherein the article of manufacture comprises the first and second compositions each separately contained as single units in a plurality of single use containers.

14. An article of manufacture for a skin-enhancing system comprising: at least first and second separately contained compositions,
(a) the first composition comprising an oxidizing component selected from the group consisting of:
(i) at least one oxidizing agent comprising hydrogen peroxide;
optionally, one or more agents selected from the group consisting of tetrasodium glutamate diacetate, tetrasodium phosphate, phosphoric acid, sodium phosphate, and combinations thereof, and water,
wherein the oxidizing component is formulated as a toner; and
(ii) at least one oxidizing agent comprising hydrogen peroxide;
at least one non-silicone oil present in the oxidizing component in a range from about 20% to about 80%, by weight, based on the total weight of the oxidizing component;
optionally, one or more agents selected from the group consisting of tetrasodium glutamate diacetate, tetrasodium phosphate, phosphoric acid, sodium phosphate, and combinations thereof, optionally, a combination of surfactants including steareth-2 and steareth-20;

optionally, one or more polymers including sclerotium gum;

optionally, one or more vitamin actives, preservatives, or combinations thereof; and water present in an amount from about 15% to about 75%, by weight, based on the weight of the oxidizing component, wherein the oxidizing component is formulated as a creamy emulsion; and (b) the second composition comprising a chemical peel component selected from the group consisting of:

(i) a plurality of hydroxy acids including at least one alpha-hydroxy acid comprising glycolic acid and at least one beta-hydroxy acid comprising salicylic acid;

at least one oil selected from the group consisting of squalane and nut oils;

one or a combination of surfactants;

one or more thickeners;

one or more water based solvents comprising glycerin;

one or more vitamin actives, preservatives, chelating agents, pH adjusters, or combinations thereof, and water present in an amount from about 40% to about 50%, by weight, based on the weight of the skin peel component, wherein the chemical peel component is formulated as a creamy emulsion; and (ii) a plurality of hydroxy acids including at least one alpha-hydroxy acid and at least one beta-hydroxy acid comprising salicylic acid;

one or a combination of oils or plant butters;

one or a combination of surfactants;

one or more thickeners including xanthan gum;

one or more water based solvents comprising glycerin or propanediol;

one or more actives, fragrances, preservatives, chelating agents, pH adjusters, or combinations thereof, and water present in an amount from about 40% to about 50%, by weight, based on the weight of the skin peel component, wherein the chemical peel component is formulated as a toner, wherein the first and second compositions are contained to be separately dispensed for application to skin, in any order, wherein at least one of the oxidizing component or the chemical peel component is a creamy emulsion, wherein the first composition is free of salicylic acid and is free of anionic polymeric associative thickeners other than hyaluronic acid, carrageenan, or combinations thereof, and may optionally include xanthan gum, carbomer, or combinations thereof, wherein the first composition is free of oxidizing agents other than the hydrogen peroxide, urea peroxide, carbamide peroxide, PVP hydrogen peroxide, or combinations thereof, wherein the second composition is free of hydrogen peroxide and free of anionic polymeric associative thickeners other than hyaluronic acid, carrageenan, or combinations thereof, and may optionally include xanthan gum, carbomer, or combinations thereof, and wherein the skin-enhancing system may be used according to any one of a number of possible application regimens wherein the oxidizing component is used in conjunction with the chemical peel component, applied in sequence, once or, or more frequently, with applications of at least one of the components on a daily basis for a few or several days.

15. The article of manufacture according to claim 14, wherein each of the first and second compositions is contained as one of a mask, liquid, stick, spray, ointment, paste, foam, mousse, shaving cream, wipe, patch, strip, or film-forming product.

16. The article of manufacture according to claim 14, wherein the first composition is an oxidizing component contained for application as a rinse-off mask, and wherein the second composition is a chemical peel component contained for application as a leave-on cream.

17. An article of manufacture for a skin-enhancing system comprising:

at least first and second separately contained compositions:

the first composition comprising an oxidizing component, comprising:

at least one oxidizing agent selected from the group consisting of hydrogen peroxide, urea peroxide, carbamide peroxide, PVP hydrogen peroxide, and combinations thereof, and water; and the second composition comprising:

a chemical peel component comprising at least one hydroxy acid; and water, wherein at least one of the first composition or the second composition is a creamy emulsion;

wherein the first and second compositions are contained to be separately dispensed for application to skin, in any order, wherein the first composition is free of salicylic acid and free of anionic polymeric associative thickeners other than hyaluronic acid, carrageenan, or combinations thereof, and may optionally include xanthan gum, carbomer or combinations thereof, wherein the first composition is free of oxidizing agents other than the hydrogen peroxide, the urea peroxide, the carbamide peroxide, the PVP hydrogen peroxide, or combinations thereof, wherein the second composition is free of hydrogen peroxide and free of anionic polymeric associative thickeners other than hyaluronic acid, carrageenan, or combinations thereof, and may optionally include xanthan gum, carbomer, or combinations thereof, and wherein the skin-enhancing system may be used according to any one of a number of possible application regimens wherein the oxidizing component is used in conjunction with the chemical peel component, applied in sequence, once or, or more frequently, with applications of at least one of the components on a daily basis for a few or several days.

18. A regimen for enhancing skin, comprising:

(a) providing a first composition comprising an oxidizing component selected from the group consisting of:

(i) at least one oxidizing agent comprising hydrogen peroxide;

optionally, one or more agents selected from the group consisting of tetrasodium glutamate diacetate, tetrasodium phosphate, phosphoric acid, sodium phosphate and combinations thereof, and water, wherein the oxidizing component is formulated as a toner; and (ii) at least one oxidizing agent comprising hydrogen peroxide;

at least one non-silicone oil present in the oxidizing component in a range from about 20% to about 80%, by weight, based on the total weight of the oxidizing component;

optionally, one or more agents selected from the group consisting of tetrasodium glutamate diacetate, tetrasodium phosphate, phosphoric acid, sodium phosphate, and combinations thereof, optionally, a combination of surfactants including steareth-2 and steareth-20;

optionally, one or more polymers including sclerotium gum;

optionally, one or more vitamin actives, preservatives or combinations thereof; and water present in an amount from about 15% to about 75%, by weight, based on the weight of the oxidizing component, wherein the oxidizing component is formulated as a creamy emulsion; and (b) providing a second composition comprising a chemical peel component selected from the group consisting of:

(i) a plurality of hydroxy acids including at least one alpha-hydroxy acid comprising glycolic acid and at least one beta-hydroxy acid comprising salicylic acid;

at least one oil selected from the group consisting of squalane and nut oils;

one or a combination of surfactants;

one or more thickeners; one or more water based solvents comprising glycerin;

one or more vitamin actives, preservatives, chelating agents, pH adjusters, or combinations thereof, and water present in an amount from about 40% to about 50%, by weight, based on the weight of the skin peel component, wherein the chemical peel component is formulated as a creamy emulsion; and (ii) a plurality of hydroxy acids including at least one alpha-hydroxy acid and at least one beta-hydroxy acid comprising salicylic acid;

one or a combination of oils or plant butters;

one or a combination of surfactants;

one or more thickeners including xanthan gum;

one or more water based solvents comprising glycerin or propanediol;

one or more actives, fragrances, preservatives, chelating agents, pH adjusters, or combinations thereof, and water present in an amount from about 40% to about 50%, by weight, based on the weight of the skin peel component, wherein the chemical peel component is formulated as a toner;

(c) applying the first composition to a region of skin excluding areas of skin around an eye; and (d) applying the first composition to a region of skin excluding areas of skin around an eye, wherein the first and second compositions are applied sequentially, in any order, wherein at least one of the oxidizing component or the chemical peel component is a creamy emulsion, wherein the first composition is free of salicylic acid and is free of anionic polymeric associative thickeners other than hyaluronic acid, xanthan gum, carrageenan, carbomer, or combinations thereof, and may optionally include xanthan gum, carbomer, or combinations thereof, wherein the first composition is free of oxidizing agents other than the hydrogen peroxide, the urea peroxide, the carbamide peroxide, the PVP hydrogen peroxide, or combinations thereof, and wherein the second composition is free of hydrogen peroxide and free of anionic polymeric associative thickeners other than hyaluronic acid, xanthan gum, carrageenan, carbomer, or combinations thereof, and may optionally include xanthan gum, carbomer, or combinations thereof.

19. The regimen in accordance with claim 18, wherein the steps of the regimen further include (e) rinsing the skin after application of at least one of the first and second compositions, and include (c), (d) and (e) in any order, and wherein the step (e) may be repeated.

20. The regimen in accordance with claim 18, wherein after a first instance of the step of applying the first composition, the step of applying the second composition is repeated once daily, over a plurality of days.

21. The regimen in accordance with claim 20, wherein (i) the step of applying the first composition is repeated once every third, fourth or fifth day and wherein the step of applying the second composition is skipped on the days that the step of applying the first composition is repeated, (ii) the regimen is practiced for at least 28 days, (iii) application of the first and second compositions according to the regimen provides synergistic benefits in stimulating cell growth and proliferation as compared with use of the first and second compositions independently, (iv) application of the first and second compositions according to the regimen results in diminished skin discomfort as compared with use of the first and second compositions independently, (v) application of the first and second compositions according to the regimen results in enhanced improvement in skin brightness as compared with use of the first and second compositions independently, (vi) or a combination of the foregoing (i)-(v).

* * * * *